(12) United States Patent
Tang et al.

(10) Patent No.: US 6,864,238 B1
(45) Date of Patent: Mar. 8, 2005

(54) METHODS AND COMPOSITIONS FOR DESTABILIZING MICROTUBULES

(75) Inventors: Tang K. Tang, Taipei (TW); Liang-Yi Hung, Kaohsiung (TW); Ching-Wen Chang, Taipei (TW)

(73) Assignee: Academia Sinica, Taipei (TW)

( * ) Notice: Subject to any disclaimer, the term of this patent is extended or adjusted under 35 U.S.C. 154(b) by 0 days.

(21) Appl. No.: 10/680,730

(22) Filed: Oct. 6, 2003

(51) Int. Cl.$^7$ .............................................. A61K 38/00
(52) U.S. Cl. ....................................... 514/12; 530/325
(58) Field of Search ............................ 514/12; 530/325

(56) References Cited

U.S. PATENT DOCUMENTS

| | | |
|---|---|---|
| 2003/0032771 A1 | 2/2003 | Sharp et al. ................. 530/324 |
| 2003/0050233 A1 | 3/2003 | Burman et al. ............... 514/12 |
| 2003/0083261 A1 | 5/2003 | Yu et al. ....................... 514/13 |

OTHER PUBLICATIONS

Belmont, L.D. and Mitchison, T.J. (1996). Identification of a protein that interacts with tubulin dimers and increases the catastrophe rate of microtubules. *Cell*, 84, 623–631.
Cassimeris, L. and Spittle, C. (2001). Regulation of microtubule–associated proteins. *Int. Rev. Cytol.*, 210, 163–226.
Cassimeris, L. (2002). The oncoprotein18/stathmin family of microtubule destabilizers. *Curr. Opin. Cell Biol.*, 14, 18–24.
Conboy, J.G., et al. (1988). Multiple protein 4.1 isoforms produced by alternative splicing in human erythroid cells. *Proc. Natl. Acad. Sci. USA*, 85, 9062–9065.
Conboy, J.G., et al. (1991). Tissue– and development–specific alternative RNA splicing regulates expression of multiple isoforms of erythroid membrane protein 4.1. *J. Biol. Chem.*, 266, 8273–8280.
DeCárcer, et al. (1995). Protein 4.1 is a component of the nuclear matrix of mammalian cells. *Biochem J.*, 312 (Pt 3) 871–877.
Desai, A., et al. (1999). Kin I kinesins are microtubule–destabilizing enzymes. *Cell*, 96, 69–78.
Erickson, H.P. and Stoffler, D. (1996). Protofilaments and rings, two conformations of the tubulin family conserved from bacterial FtsZ to α/β and γ tubulin. *J. Cell Biol.*, 135, 5–8.
Hartman, J.J., et al. (1998). Katanin, a microtubule–severing protein, is a novel AAA ATPase that targets to the centrosome using a WD40–containing subunit. *Cell*, 93, 277–287.
Heald, R. and Nogales, E. (2002). Microtubule dynamics. *J Cell Sci*, 115, 3–4.
Huang, J.P., et al. (1993). Genomic structure of the locus encoding protein 4.1. Structural basis for complex combinational patterns of tissue–specific alternative RNA splicing. *J. Biol. Chem.*, 268, 3758–3766.
Hung, L.Y., et al. (2000). Protein 4.1 R–135 interacts with a novel centrosomal protein (CPAP) which is associated with the γ–tubulin complex. *Mol. Cell Biol.*, 20, 7813–7825.
Hung, L.Y. and Tang, T.K. (2002). A novel centrosomal protein (CPAP) play a role in cell mitosis and genomic stability. P. 115, Program & Abstracts, the 4$^{th}$ Asian–Pacific Organization for Cell Biology Congress, Nov. 3–6, 2002.
Krauss, S.W., et al. (1997). Structural protein 4.1 in the nucleus of human cells: dynamic rearrangements during cell division. *J. Cell Biol.*, 137, 275–289.
Krauss, S.W., et al. (1997). Structural protein 4.1 is located in mammalian centrosomes. *Proc. Natl. Acad. Sci. USA*, 94, 7297–7302.
Mattagajasingh, S.N., et al. (1999). A nonerythroid isoform of protein 4.1R interacts with the nuclear mitotic apparatus (NuMA) protein. *J. Cell Biol.*, 145, 29–43.
McCabe, P.M., et al. (1999). The influence of dsRNA viruses on the biology of plant pathogenic fungi. *Trends Microbial.* 7:377–81.
McNally, F.J. and Vale, R.D. (1993). Identification of katanin, an ATPase that severs and disassembles stable microtubules. *Cell*, 75, 419–429.
Peng, B., et al. (2002). CPAP is a novel stat5–interacting cofactor that augments stat5–mediated transcriptional activity. *Mol. Endocrinol.*, 16, 2019–2033.
Pérez–Ferreiro, C.M., et al. (2001). 4.1R proteins associate with interphase microtubules in human T cells: a 4.1R constitutive region is involved in tubulin binding. *J. Biol. Chem.*, 276, 44785–44791.
Rao, J.S. (2003). Molecular mechanisms of glioma invasiveness: the role of proteases. *Nat. Rev. Cancer*, 3:489–501.
Rochefort, H., et al. (1990). Cathepsin D in breast cancer: from molecular and cellular biology to clinical applications. *Cancer Cells*, 2:383–88.
Schiebel, E. (2000). γ–tubulin complexes: binding to the centrosome, regulation and microtubule nucleation. *Curr. Opin. Cell Biol.*, 12, 113–118.
Tang, T.K., et al. (1988). Selective expression of an erythroid–specific isoform of protein 4.1. *Proc. Natl. Acad. Sci. USA*, 85, 3713–3717.
Tang, T.K., et al. (1990). Heterogeneity of mRNA and protein products arising from the protein 4.1 gene in erythroid and nonerythroid tissues. *J. Cell Biol.*, 110, 617–624.
Todd, S., et al. (2000). HIV protease as a target for retrovirus vector–mediated gene therapy. *Biochim. Biophys. Acta.*, 1477(12):168–188.
Walczak, C.E., et al. (1996). XKCM1: a Xenopus kinesin–related protein that regulates microtubule dynamics during mitotic spindle assembly. *Cell*, 84, 37–47.
Zheng, Y., et al. (1995). Nucleation of microtubule assembly by a γ–tubulin–containing ring complex. *Nature*, 378, 578–583.

*Primary Examiner*—Robert A. Wax
*Assistant Examiner*—Suzanne M. Mayer
(74) *Attorney, Agent, or Firm*—Fish & Richardson P.C.

(57) ABSTRACT

Polypeptides that comprise an approximately 100-amino acid residue region of a centrosomal P4.1-associated protein (CPAP) that possess microtubule-destabilizing activity, polynucleotides encoding such polypeptides, compositions comprising the polypeptides and polynucleotides, and methods of use thereof, are disclosed. The invention is useful for destabilizing microtubules in eukaryotic cells, including but not limited to cancer cells.

6 Claims, 9 Drawing Sheets

(F)
```
              327                341                   362
               |                  |                     |
     wt      IKAA IGERKQTFED YLEEQIQLEE QELKQKQLKE AE
     341P    ---- ---------- p--------- ---------- --    0.01
     346P    ---- ---------- -----p---- ---------- --    0.06
     348P    ---- ---------- -------p-- ---------- --    0.00
     353P    ---- ---------- ---------- --p------- --    0.06
```

(G)

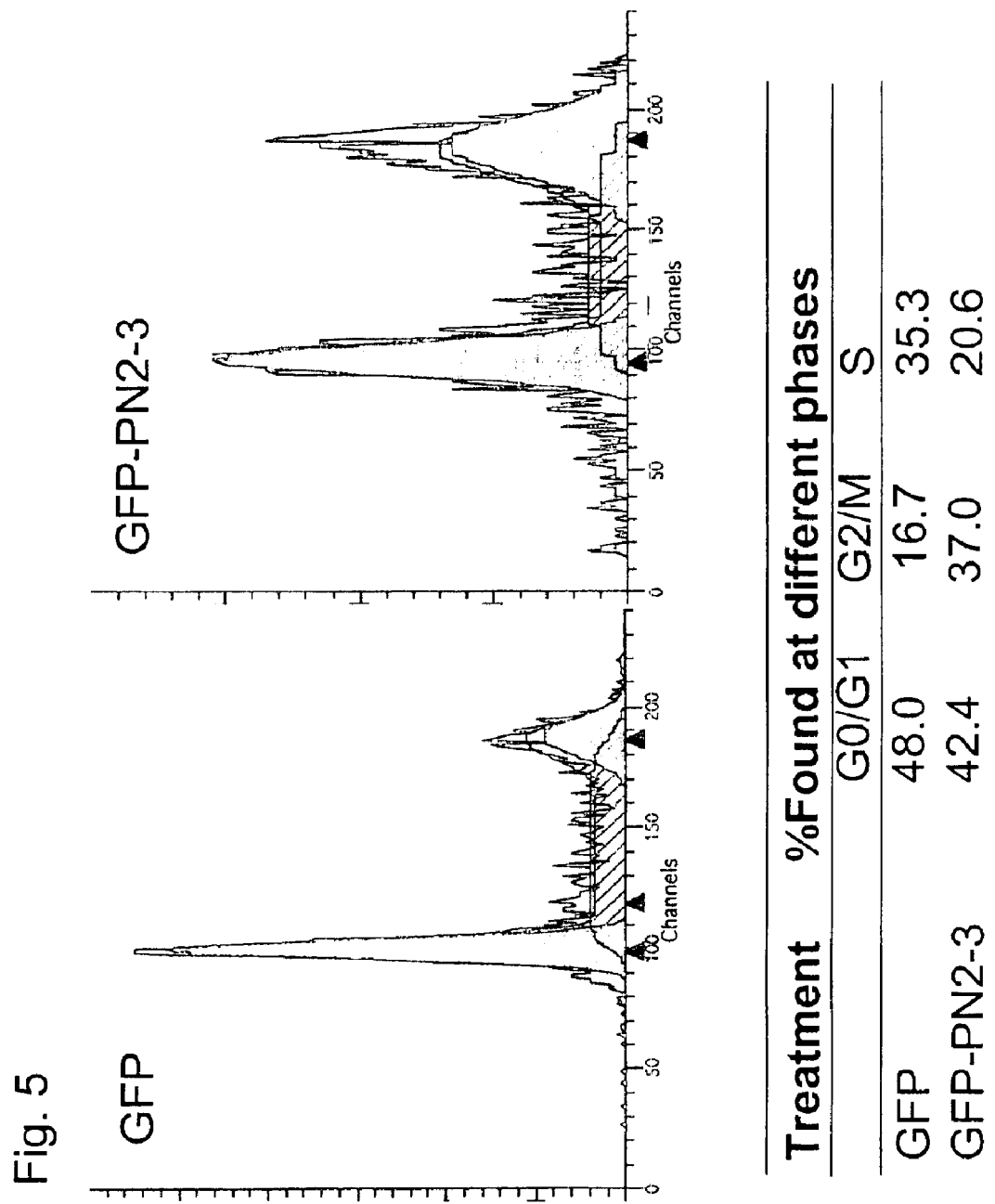

Fig. 6 (SEQ ID NO:1)

```
   1 MFLMPTSSEL NSGQNFLTQW MTNPSRAGVI LNRGFPILEA DKEKRAAVDI STSFPIKGTH
  61 FSDSFSFINE EDSLLEEQKL ESNNPYKPQS DKSETHTAFP CIKKGPQVAA CHSAPGHQEE
 121 NKNDFIPDRA SEFKEGAYKD PLFKKLEQLK EVQQKKQEQL KRQQLEQLQR LMEEQEKLLT
 181 MVSGQCTLPG LSLLPDDQSQ KHRSPGNTTT GERATCCFPS YVYPDPTQEE TYPSNILSHE
 241 QSNFCRTAHG DFVLTSKRAS PNLFSEAQYQ EAPVEKNNLK EENRNHPTGE SILCWEKVTE
 301 QIQEANDKNL QKHDDSSEVA NIEERPIKAA IGERKQTFED YLEEQIQLEE QELKQKQLKE
 361 AEGPLPIKAK PKQPFLKRGE GLARFTNAKS KFQKGKESKL VTNQSTSEDQ PLFKMDRQQL
 421 QRKTALKNKE LCADNPILKK DSKARTKSGS VTLSQKPKML KCSNRKSLSP SGLKIQTGKK
 481 CDGQFRDQIK FENKVTSNNK ENVTECPKPC DTGCTGWNKT QGKDRLPLST GPASRLAAKS
 541 PIRETMKESE SSLDVSLQKK LETWEREKEK ENLELDEFLF LEQAADEISF SSNSSFVLKI
 601 LERDQQICKG HRMSSTPVKA VPQKTNPADP ISHCNRSEDL DHTAREKESE CEVAPKQLHS
 661 LSSADELREQ PCKIRKAVQK STSENQTEWN ARDDEGVPNS DSSTDSEEQL DVTIKPSTED
 721 RERGISSRED SPQVCDDKGP FKDTRTQEDK RRDVDLDLSD KDYSSDESIM ESIKHKVSEP
 781 SRSSSLSLSK MDFDDERTWT DLEENLCNHD VVLGNESTYG TPQTCYPNNE IGILDKTIKR
 841 KIAPVKRGED LSKSRRSRSP PTSELMMKFF PSLKPKPKSD SHLGNELKLN ISQDQPPGDN
 901 ARSQVLREKI IELETEIEKF KAENASLAKL RIERESALEK LRKEIADFEQ QKAKELARIE
 961 EFKKEEMRKL QKERKVFEKY TTAARTFPDK KEREEIQTLK QQIADLREDL KRKETKWSST
1021 HSRLRSQIQM LVRENTDLRE EIKVMERFRL DAWKRAEAIE SSLEVEKKDK LANTSVRFQN
1081 SQISSGTQVE KYKKNYLPMQ GNPPRRSKSA PPRDLGNLDK GQAASPREPL EPLNFPDPEY
1141 KEEEEDQDIQ GEISHPDGKV EKVYKNGCRV ILFPNGTRKE VSADGKTITV TFFNGDVKQV
1201 MPDQRVIYYY AAAQTTHTTY PEGLEVLHFS SGQIEKHYPD GRKEITFPDQ TVKNLFPDGQ
1261 EESIFPDGTI VRVQRDGNKL IEFNNGQREL HTAQFKRREY PDGTVKTVYA NGHQETKYRS
1321 GRIRVKDKEG NVSMDTEL
```

Fig. 7 (SEQ ID NO:2)

```
   1 cggcccgagg tcctgtggga agtgaggatc tcaggacggg ggcggggctc cgacagaggc
  61 ggcgattgtg gcggcccatt tgtaaatgct gcggagattg aggtgtcggt tcgtgctgct
 121 gagctgccca ggcttcacgg agcggtgttg gtaatcaata gctcttctag cctttgcatt
 181 gtttaaatat aatagtgtca ttggactaag atgttcctga tgccaacctc ttcagagtta
 241 aacagtgggc agaacttcct aacccagtgg atgaccaatc cttctcgggc tggggtcata
 301 ttaaatcgtg gatttcctat tttgaagca gacaagaga agcgagcagc tgtggacatt
 361 tctaccagct ttcctattaa aggcacacat ttttctgata gcttcagctt tataaatgaa
 421 gaagattcac ttcttgaaga acagaagttg gagtcaaaca acccttacaa accacagtca
 481 gataaatctg aaacccatac agcctttcct tgcattaaaa agggaccaca ggtagcggca
 541 tgtcacagtg ctcctggaca ccaggaagaa aacaaaaatg acttcatccc agatcgtgcg
 601 agtgaattca agaagggggc ttataaagac ccactttta aaaaacttga acagctgaaa
 661 gaagtacaac agaagaagca ggaacaattg aagaggcaac agttggagca actacagaga
 721 ctcatggaag aacaagagaa gctgctcacc atggtgtctg ggcagtgcac acttccaggt
 781 ttgagtttac tgcctgatga tcagagccag aagcacaggt ctccaggaaa taccaccact
 841 ggagagagag ccacatgctg cttcccatca tatgtctacc cggacccaac ccaggaagaa
 901 acatacccgt ccaacatttt atcccatgag caaagcaact tctgtagaac tgctcatgga
 961 gattttgtct taacttcaaa acgtgcgtct cctaatttat tttctgaggc acagtatcaa
1021 gaagcacctg tggaaaaaaa taatttaaaa gaagaaaacc gtaaccatcc tacaggagaa
1081 agtatcttat gttgggagaa agtgacagaa cagattcagg aagcaaatga taagaactta
1141 caaaaacatg atgattcctc agaagtggct aatattgaag aaaggcccat taaagctgct
1201 attggagaaa ggaaacagac ctttgaagat tacttagaag aacaaattca gttggaagag
1261 caagaactga agcaaaaaca gctgaaggaa gcagaaggac cattgccaat caaagcaaaa
1321 ccaaaacaac cattttaaa acgaggagaa ggtttagcta gatttactaa tgccaaatct
1381 aagtttcaaa aaggcaaaga aagtaaacta gtgactaacc agcacttc cgaggaccag
1441 ccgctgttta aaatggatag acagcaactc cagcggaaaa ccgctcttaa aaataaagag
1501 ctgtgtgcag acaaccctat ccttaaaaag gacagtaaag ctagaaccaa gagtggttct
1561 gtcaccctca gtcagaagcc gaaaatgctg aagtgtagta acaggaaaag tctttctccg
1621 tcaggattga aaatacagac ggggaagaaa tgtgatgggc agtttagaga ccagatcaaa
1681 tttgaaaaca aagtcacatc taataataaa gaaaatgtaa ctgagtgtcc aaaaccttgc
1741 gatactggct gcacagggtg gaataagaca caaggtaaag acagacttcc tctttcaaca
1801 gggccggcca gcggctggc tgctaagagc cccataaggg agaccatgaa agagtctgaa
1861 tcttctcttg acgtttctct tcagaaaaag ttagagactt gggaacgaga aaaggaaaag
1921 gaaaatttgg aattagatga attttgttt ttagaacaag ctgctgatga aatatcattt
1981 tctagtaatt cctcatttgt actgaaaatc ttagaaaggg atcaacagat ctgcaaaggt
2041 caccggatgt cttccacccc tgtcaaagct gtgccacaga agacaaatcc ggcagatccc
2101 attagtcatt gtaaccgcag tgaggatttg gaccacactg cacgtgagaa ggagagtgag
2161 tgtgaagtcg cacccaaaca acttcattca ttgtcctcag ctgatgaatt gagggaacag
2221 ccttgtaaaa tcaggaaagc cgtccaaaag agcacttctg aaaatcagac tgaatggaat
2281 gcacgtgacg atgaaggtgt tccaaatagt gacagtagca ctgactctga ggaacagctt
2341 gatgttacca taaaaccatc gactgaggat agagagaggg gcatcagcag cagagaggat
2401 agcccacaag tctgtgatga taggggcct tttaaggaca ccaggaccca agaagataaa
2461 aggagagatg ttgatctgga tttgtctgat aaagattaca gtagcgatga gtctatcatg
2521 gaaagcataa aacataaagt gtctgagccc tcgagatcct catccctaag tctgagtaaa
2581 atggactttg atgatgaaag aacttggact gaccttgaag agaatttgtg taaccatgat
2641 gttgttcttg gaatgaatc cacttatggg acgccgcaga catgctaccc taataatgaa
2701 ataggtatcc tggacaaaac aataaaaagg aagattgcac cagtcaagag gggagaagac
2761 ttgagcaagt ccaggaggag cagaagtcct cctacatcgg agctgatgat gaaattcttt
2821 ccttctttga aaccaaaacc aaagtcagat tcacacttgg gaaatgaact caagttaaac
2881 ataagtcaag accaaccacc tggtgacaat gctcgatccc aggttttgag agagaaaatt
2941 attgaattgg aaacagaaat agaaagttt aagctgaga acgcatcttt agctaaactt
3001 cgcattgaac gagaaagtgc cttggaaaaa ctcaggaaag aaattgcaga cttcgaacaa
3061 cagaaagcaa aagaattagc tcgaatagaa gagtttaaaa aggaggagat gaggaagcta
3121 caaaaggaac gtaaagtttt tgaaaagtat actacagctg caagaacttt tccagataaa
3181 aggaacgtg aagaaataca gactttaaaa cagcaaatag cagatttacg ggaagatttg
3241 aaaagaaagg agaccaaatg gtcaagtaca cacagccgtc tcagaagcca gatacaaatg
3301 ttagtcagag agaacacaga cctccgggaa gaaataaaag tgatgaaaag attccgactg
3361 gatgcctgga agagagcaga agccatagag agcagcctcg aggtggagaa gaaggacaag
```

```
3421 cttgcgaaca catctgttcg atttcaaaac agtcagattt cttcaggaac ccaggtagaa
3481 aaatacaaga aaaattatct tccaatgcaa ggcaatccac ctcgaagatc caagtctgca
3541 cctcctcgtg atttaggcaa tttggataag ggacaagctg cctctcccag ggagccactt
3601 gaaccactga acttcccaga tcctgaatat aaagaggagg aggaagacca agacatacag
3661 ggagaaatca gtcatcctga tggaaaggtg gaaaaggttt ataagaatgg gtgccgtgtt
3721 atactgtttc ccaatggaac tcgaaaggaa gtgagtgcag atgggaagac catcactgtc
3781 actttcttta atggtgacgt gaagcaggtc atgccagacc aaagagtgat ttactactat
3841 gcagctgccc agaccactca cacgacatac ccggagggac tggaagtttt acatttttca
3901 agtggacaaa tagaaaaaca ttacccagat ggaaggaaag aaatcacgtt tcctgaccag
3961 actgttaaaa acttatttcc tgatggacaa gaagaaagca ttttcccaga tggtacaatt
4021 gtcagagtac aacgtgatgg caacaaactc atagagttta ataatggcca aagagaacta
4081 catactgccc agttcaagag acgggaatac ccagatggca ctgttaaaac cgtatatgca
4141 aacggtcatc aagaaacgaa gtacagatcc ggtcggataa gagttaagga caaggagggt
4201 aatgtgtcaa tggacacgga gctgtgacga tcctcatgtg atcatgaagt aacagtaact
4261 gacttttat gttaaaaaat gtacatttac tgtggattct gtttaattta ttgtgtatgt
4321 gtggggaaaa gattggattt taaaataaaa gtttaccctg tggcattttc aaaaaaaaaa
4381 aaaaaa
```

(Fig. 7 continued)

SEQUENCE LISTING

<160> NUMBER OF SEQ ID NOS: 3

<210> SEQ ID NO 1
<211> LENGTH: 1338
<212> TYPE: PRT
<213> ORGANISM: Homo sapiens

<400> SEQUENCE: 1

```
Met Phe Leu Met Pro Thr Ser Ser Glu Leu Asn Ser Gly Gln Asn Phe
1               5                   10                  15

Leu Thr Gln Trp Met Thr Asn Pro Ser Arg Ala Gly Val Ile Leu Asn
                20                  25                  30

Arg Gly Phe Pro Ile Leu Glu Ala Asp Lys Glu Lys Arg Ala Ala Val
            35                  40                  45

Asp Ile Ser Thr Ser Phe Pro Ile Lys Gly Thr His Phe Ser Asp Ser
    50                  55                  60

Phe Ser Phe Ile Asn Glu Glu Asp Ser Leu Leu Glu Glu Gln Lys Leu
65                  70                  75                  80

Glu Ser Asn Asn Pro Tyr Lys Pro Gln Ser Asp Lys Ser Glu Thr His
                85                  90                  95

Thr Ala Phe Pro Cys Ile Lys Lys Gly Pro Gln Val Ala Ala Cys His
            100                 105                 110

Ser Ala Pro Gly His Gln Glu Glu Asn Lys Asn Asp Phe Ile Pro Asp
        115                 120                 125

Arg Ala Ser Glu Phe Lys Glu Gly Ala Tyr Lys Asp Pro Leu Phe Lys
    130                 135                 140

Lys Leu Glu Gln Leu Lys Glu Val Gln Gln Lys Lys Gln Glu Gln Leu
145                 150                 155                 160

Lys Arg Gln Gln Leu Glu Gln Leu Gln Arg Leu Met Glu Glu Gln Glu
                165                 170                 175

Lys Leu Leu Thr Met Val Ser Gly Gln Cys Thr Leu Pro Gly Leu Ser
            180                 185                 190

Leu Leu Pro Asp Asp Gln Ser Gln Lys His Arg Ser Pro Gly Asn Thr
        195                 200                 205

Thr Thr Gly Glu Arg Ala Thr Cys Cys Phe Pro Ser Tyr Val Tyr Pro
    210                 215                 220

Asp Pro Thr Gln Glu Glu Thr Tyr Pro Ser Asn Ile Leu Ser His Glu
225                 230                 235                 240

Gln Ser Asn Phe Cys Arg Thr Ala His Gly Asp Phe Val Leu Thr Ser
                245                 250                 255

Lys Arg Ala Ser Pro Asn Leu Phe Ser Glu Ala Gln Tyr Gln Glu Ala
            260                 265                 270

Pro Val Glu Lys Asn Asn Leu Lys Glu Glu Asn Arg Asn His Pro Thr
        275                 280                 285
```

-continued

Gly Glu Ser Ile Leu Cys Trp Glu Lys Val Thr Glu Gln Ile Gln Glu
    290                 295                 300

Ala Asn Asp Lys Asn Leu Gln Lys His Asp Asp Ser Ser Glu Val Ala
305                 310                 315                 320

Asn Ile Glu Glu Arg Pro Ile Lys Ala Ala Ile Gly Glu Arg Lys Gln
                325                 330                 335

Thr Phe Glu Asp Tyr Leu Glu Glu Gln Ile Gln Leu Glu Glu Gln Glu
            340                 345                 350

Leu Lys Gln Lys Gln Leu Lys Glu Ala Glu Gly Pro Leu Pro Ile Lys
        355                 360                 365

Ala Lys Pro Lys Gln Pro Phe Leu Lys Arg Gly Glu Gly Leu Ala Arg
370                 375                 380

Phe Thr Asn Ala Lys Ser Lys Phe Gln Lys Gly Lys Ser Lys Leu
385                 390                 395                 400

Val Thr Asn Gln Ser Thr Ser Glu Asp Gln Pro Leu Phe Lys Met Asp
                405                 410                 415

Arg Gln Gln Leu Gln Arg Lys Thr Ala Leu Lys Asn Lys Glu Leu Cys
            420                 425                 430

Ala Asp Asn Pro Ile Leu Lys Lys Asp Ser Lys Ala Arg Thr Lys Ser
        435                 440                 445

Gly Ser Val Thr Leu Ser Gln Lys Pro Lys Met Leu Lys Cys Ser Asn
450                 455                 460

Arg Lys Ser Leu Ser Pro Ser Gly Leu Lys Ile Gln Thr Gly Lys Lys
465                 470                 475                 480

Cys Asp Gly Gln Phe Arg Asp Gln Ile Lys Phe Glu Asn Lys Val Thr
                485                 490                 495

Ser Asn Asn Lys Glu Asn Val Thr Glu Cys Pro Lys Pro Cys Asp Thr
            500                 505                 510

Gly Cys Thr Gly Trp Asn Lys Thr Gln Gly Lys Asp Arg Leu Pro Leu
        515                 520                 525

Ser Thr Gly Pro Ala Ser Arg Leu Ala Ala Lys Ser Pro Ile Arg Glu
530                 535                 540

Thr Met Lys Glu Ser Glu Ser Ser Leu Asp Val Ser Leu Gln Lys Lys
545                 550                 555                 560

Leu Glu Thr Trp Glu Arg Glu Lys Glu Lys Glu Asn Leu Glu Leu Asp
                565                 570                 575

Glu Phe Leu Phe Leu Glu Gln Ala Ala Asp Glu Ile Ser Phe Ser Ser
            580                 585                 590

Asn Ser Ser Phe Val Leu Lys Ile Leu Glu Arg Asp Gln Gln Ile Cys
        595                 600                 605

Lys Gly His Arg Met Ser Ser Thr Pro Val Lys Ala Val Pro Gln Lys
610                 615                 620

Thr Asn Pro Ala Asp Pro Ile Ser His Cys Asn Arg Ser Glu Asp Leu
625                 630                 635                 640

Asp His Thr Ala Arg Glu Lys Glu Ser Glu Cys Glu Val Ala Pro Lys
                645                 650                 655

Gln Leu His Ser Leu Ser Ser Ala Asp Glu Leu Arg Glu Gln Pro Cys
            660                 665                 670

Lys Ile Arg Lys Ala Val Gln Lys Ser Thr Ser Glu Asn Gln Thr Glu
        675                 680                 685

Trp Asn Ala Arg Asp Asp Glu Gly Val Pro Asn Ser Asp Ser Ser Thr
690                 695                 700

-continued

```
Asp Ser Glu Glu Gln Leu Asp Val Thr Ile Lys Pro Ser Thr Glu Asp
705                 710                 715                 720

Arg Glu Arg Gly Ile Ser Ser Arg Glu Asp Ser Pro Gln Val Cys Asp
                725                 730                 735

Asp Lys Gly Pro Phe Lys Asp Thr Arg Thr Gln Glu Asp Lys Arg Arg
            740                 745                 750

Asp Val Asp Leu Asp Leu Ser Asp Lys Asp Tyr Ser Ser Asp Glu Ser
        755                 760                 765

Ile Met Glu Ser Ile Lys His Lys Val Ser Glu Pro Ser Arg Ser Ser
    770                 775                 780

Ser Leu Ser Leu Ser Lys Met Asp Phe Asp Asp Glu Arg Thr Trp Thr
785                 790                 795                 800

Asp Leu Glu Glu Asn Leu Cys Asn His Asp Val Val Leu Gly Asn Glu
                805                 810                 815

Ser Thr Tyr Gly Thr Pro Gln Thr Cys Tyr Pro Asn Asn Glu Ile Gly
            820                 825                 830

Ile Leu Asp Lys Thr Ile Lys Arg Lys Ile Ala Pro Val Lys Arg Gly
        835                 840                 845

Glu Asp Leu Ser Lys Ser Arg Arg Ser Arg Ser Pro Pro Thr Ser Glu
    850                 855                 860

Leu Met Met Lys Phe Phe Pro Ser Leu Lys Pro Lys Pro Lys Ser Asp
865                 870                 875                 880

Ser His Leu Gly Asn Glu Leu Lys Leu Asn Ile Ser Gln Asp Gln Pro
                885                 890                 895

Pro Gly Asp Asn Ala Arg Ser Gln Val Leu Arg Glu Lys Ile Ile Glu
            900                 905                 910

Leu Glu Thr Glu Ile Glu Lys Phe Lys Ala Glu Asn Ala Ser Leu Ala
        915                 920                 925

Lys Leu Arg Ile Glu Arg Glu Ser Ala Leu Glu Lys Leu Arg Lys Glu
    930                 935                 940

Ile Ala Asp Phe Glu Gln Gln Lys Ala Lys Glu Leu Ala Arg Ile Glu
945                 950                 955                 960

Glu Phe Lys Lys Glu Glu Met Arg Lys Leu Gln Lys Glu Arg Lys Val
                965                 970                 975

Phe Glu Lys Tyr Thr Thr Ala Ala Arg Thr Phe Pro Asp Lys Lys Glu
            980                 985                 990

Arg Glu Glu Ile Gln Thr Leu Lys Gln Gln Ile Ala Asp Leu Arg Glu
        995                 1000                1005

Asp Leu Lys Arg Lys Glu Thr Lys Trp Ser Ser Thr His Ser Arg Leu
    1010                1015                1020

Arg Ser Gln Ile Gln Met Leu Val Arg Glu Asn Thr Asp Leu Arg Glu
1025                1030                1035                1040

Glu Ile Lys Val Met Glu Arg Phe Arg Leu Asp Ala Trp Lys Arg Ala
                1045                1050                1055

Glu Ala Ile Glu Ser Ser Leu Glu Val Glu Lys Lys Asp Lys Leu Ala
            1060                1065                1070

Asn Thr Ser Val Arg Phe Gln Asn Ser Gln Ile Ser Ser Gly Thr Gln
        1075                1080                1085

Val Glu Lys Tyr Lys Lys Asn Tyr Leu Pro Met Gln Gly Asn Pro Pro
    1090                1095                1100

Arg Arg Ser Lys Ser Ala Pro Pro Arg Asp Leu Gly Asn Leu Asp Lys
1105                1110                1115                1120

Gly Gln Ala Ala Ser Pro Arg Glu Pro Leu Glu Pro Leu Asn Phe Pro
```

-continued

```
                1125                1130                1135
Asp Pro Glu Tyr Lys Glu Glu Glu Asp Gln Asp Ile Gln Gly Glu
            1140                1145                1150

Ile Ser His Pro Asp Gly Lys Val Glu Lys Val Tyr Lys Asn Gly Cys
            1155                1160                1165

Arg Val Ile Leu Phe Pro Asn Gly Thr Arg Lys Glu Val Ser Ala Asp
        1170                1175                1180

Gly Lys Thr Ile Thr Val Thr Phe Phe Asn Gly Asp Val Lys Gln Val
1185                1190                1195                1200

Met Pro Asp Gln Arg Val Ile Tyr Tyr Tyr Ala Ala Ala Gln Thr Thr
            1205                1210                1215

His Thr Thr Tyr Pro Glu Gly Leu Glu Val Leu His Phe Ser Ser Gly
            1220                1225                1230

Gln Ile Glu Lys His Tyr Pro Asp Gly Arg Lys Glu Ile Thr Phe Pro
            1235                1240                1245

Asp Gln Thr Val Lys Asn Leu Phe Pro Asp Gly Gln Glu Glu Ser Ile
        1250                1255                1260

Phe Pro Asp Gly Thr Ile Val Arg Val Gln Arg Asp Gly Asn Lys Leu
1265                1270                1275                1280

Ile Glu Phe Asn Asn Gly Gln Arg Glu Leu His Thr Ala Gln Phe Lys
            1285                1290                1295

Arg Arg Glu Tyr Pro Asp Gly Thr Val Lys Thr Val Tyr Ala Asn Gly
            1300                1305                1310

His Gln Glu Thr Lys Tyr Arg Ser Gly Arg Ile Arg Val Lys Asp Lys
            1315                1320                1325

Glu Gly Asn Val Ser Met Asp Thr Glu Leu
        1330                1335
```

<210> SEQ ID NO 2
<211> LENGTH: 4387
<212> TYPE: DNA
<213> ORGANISM: Homo sapiens

<400> SEQUENCE: 2

| | |
|---|---|
| cggcccgagg tcctgtggga agtgaggatc tcaggacggg ggcggggctc cgacagaggc | 60 |
| ggcgattgtg gcggcccatt tgtaaatgct gcggagattg aggtgtcggt tcgtgctgct | 120 |
| gagctgccca ggcttcacgg agcggtgttg gtaatcaata gctcttctag cctttgcatt | 180 |
| gtttaaatat aatagtgtca ttggactaag atgttcctga tgccaacctc ttcagagtta | 240 |
| aacagtgggc agaacttcct aacccagtgg atgaccaatc cttctcgggc tggggtcata | 300 |
| ttaaatcgtg gatttcctat tttggaagca gacaaagaga agcgagcagc tgtgacatt | 360 |
| tctaccagct ttcctattaa aggcacacat ttttctgata gcttcagctt tataaatgaa | 420 |
| gaagattcac ttcttgaaga acagaagttg gagtcaaaca acccttacaa accacagtca | 480 |
| gataaatctg aaacccatac agcctttcct tgcattaaaa agggaccaca ggtagcggca | 540 |
| tgtcacagtg ctcctggaca ccaggaagaa aacaaaatg acttcatccc agatcgtgcg | 600 |
| agtgaattca agaaggggc ttataaagac ccactttta aaaacttga acagctgaaa | 660 |
| gaagtacaac agaagaagca ggaacaattg aagaggcaac agttggagca actacagaga | 720 |
| ctcatggaag aacaagagaa gctgctcacc atggtgtctg ggcagtgcac acttccaggt | 780 |
| ttgagtttac tgcctgatga tcagagccag aagcacaggt ctccaggaaa taccaccact | 840 |
| ggagagagag ccacatgctg cttcccatca tatgtctacc cggacccaac ccaggaagaa | 900 |

```
acatacccgt ccaacatttt atcccatgag caaagcaact tctgtagaac tgctcatgga    960
gattttgtct taacttcaaa acgtgcgtct cctaatttat tttctgaggc acagtatcaa   1020
gaagcacctg tggaaaaaaa taatttaaaa gaagaaaacc gtaaccatcc tacaggagaa   1080
agtatcttat gttgggagaa agtgacagaa cagattcagg aagcaaatga taagaactta   1140
caaaaacatg atgattcctc agaagtggct aatattgaag aaaggcccat taaagctgct   1200
attggagaaa ggaaacagac ctttgaagat tacttagaag aacaaattca gttggaagag   1260
caagaactga agcaaaaaca gctgaaggaa gcagaaggac cattgccaat caaagcaaaa   1320
ccaaaacaac cattttttaaa acgaggagaa ggtttagcta gatttactaa tgccaaatct   1380
aagtttcaaa aaggcaaaga aagtaaacta gtgactaacc agagcacttc cgaggaccag   1440
ccgctgttta aaatggatag acagcaactc cagcggaaaa ccgctcttaa aaataaagag   1500
ctgtgtgcag acaaccctat ccttaaaaag gacagtaaag ctagaaccaa gagtggttct   1560
gtcaccctca gtcagaagcc gaaaatgctg aagtgtagta acaggaaaag tctttctccg   1620
tcaggattga aaatacagac ggggaagaaa tgtgatgggc agtttagaga ccagatcaaa   1680
tttgaaaaca aagtcacatc taataataaa gaaaatgtaa ctgagtgtcc aaaaccttgc   1740
gatactggct gcacagggtg gaataagaca caaggtaaag acagacttcc tctttcaaca   1800
gggccggcca gccggctggc tgctaagagc cccataaggg agaccatgaa agagtctgaa   1860
tcttctcttg acgtttctct tcagaaaaag ttagagactt gggaacgaga aaaggaaaag   1920
gaaaatttgg aattagatga attttttgttt ttagaacaag ctgctgatga atatcatttt   1980
tctagtaatt cctcatttgt actgaaaatc ttagaaaggg atcaacagat ctgcaaaggt   2040
caccggatgt cttccacccc tgtcaaagct gtgccacaga agacaaatcc ggcagatccc   2100
attagtcatt gtaaccgcag tgaggatttg gaccacactg cacgtgagaa ggagagtgag   2160
tgtgaagtcg cacccaaaca acttcattca ttgtcctcag ctgatgaatt gagggaacag   2220
ccttgtaaaa tcaggaaagc cgtccaaaag agcacttctg aaaatcagac tgaatggaat   2280
gcacgtgacg atgaaggtgt tccaaatagt gacagtagca ctgactctga ggaacagctt   2340
gatgttacca taaaaccatc gactgaggat agagagaggg gcatcagcag cagagaggat   2400
agcccacaag tctgtgatga taaggggcct tttaaggaca ccaggaccca agaagataaa   2460
aggagagatg ttgatctgga tttgtctgat aaagattaca gtagcgatga gtctatcatg   2520
gaaagcataa aacataaagt gtctgagccc tcgagatcct catccctaag tctgagtaaa   2580
atggactttg atgatgaaag aacttggact gaccttgaag agaatttgtg taaccatgat   2640
gttgttcttg ggaatgaatc cacttatggg acgccgcaga catgctaccc taataatgaa   2700
ataggtatcc tggacaaaac aataaaaagg aagattgcac cagtcaagag gggagaagac   2760
ttgagcaagt ccaggaggag cagaagtcct cctacatcgg agctgatgat gaaattcttt   2820
ccttctttga aaccaaaaacc aaagtcagat tcacacttgg gaaatgaact caagttaaac   2880
ataagtcaag accaaccacc tggtgacaat gctcgatccc aggttttgag agagaaaatt   2940
attgaattgg aaacagaaat agaaaagttt aaagctgaga acgcatcttt agctaaactt   3000
cgcattgaac gagaaagtgc cttggaaaaa ctcaggaaag aaattgcaga cttcgaacaa   3060
cagaaagcaa aagaattagc tcgaatagaa gagtttaaaa aggaggagat gaggaagcta   3120
caaaaggaac gtaaagtttt tgaaaagtat actacagctg caagaacttt tccagataaa   3180
aaggaacgtg aagaaataca gactttaaaa cagcaaatag cagatttacg ggaagatttg   3240
aaaagaaagg agaccaaatg gtcaagtaca cacagccgtc tcagaagcca gatacaaatg   3300
```

-continued

```
ttagtcagag agaacacaga cctccgggaa gaaataaaag tgatggaaag attccgactg    3360
gatgcctgga agagagcaga agccatagag agcagcctcg aggtggagaa gaaggacaag    3420
cttgcgaaca catctgttcg atttcaaaac agtcagattt cttcaggaac ccaggtagaa    3480
aaatacaaga aaaattatct tccaatgcaa ggcaatccac ctcgaagatc caagtctgca    3540
cctcctcgtg atttaggcaa tttggataag ggacaagctg cctctcccag ggagccactt    3600
gaaccactga acttcccaga tcctgaatat aaagaggagg aggaagacca agacatacag    3660
ggagaaatca gtcatcctga tggaaaggtg gaaaaggttt ataagaatgg gtgccgtgtt    3720
atactgtttc ccaatggaac tcgaaaggaa gtgagtgcag atgggaagac catcactgtc    3780
actttcttta atggtgacgt gaagcaggtc atgccagacc aaagagtgat ttactactat    3840
gcagctgccc agaccactca cacgacatac ccggagggac tggaagtttt acatttttca    3900
agtggacaaa tagaaaaaca ttacccagat ggaaggaaag aaatcacgtt tcctgaccag    3960
actgttaaaa acttatttcc tgatggacaa gaagaaagca tttccccaga tggtacaatt    4020
gtcagagtac aacgtgatgg caacaaactc atagagttta ataatggcca aagagaacta    4080
catactgccc agttcaagag acgggaatac ccagatggca ctgttaaaac cgtatatgca    4140
aacggtcatc aagaaacgaa gtacagatcc ggtcggataa gagttaagga caaggagggt    4200
aatgtgtcaa tggacacgga gctgtgacga tcctcatgtg atcatgaagt aacagtaact    4260
gactttttat gttaaaaaat gtacatttac tgtggattct gtttaattta ttgtgtatgt    4320
gtggggaaaa gattggattt taaaataaaa gtttaccctg tggcattttc aaaaaaaaaa    4380
aaaaaaa                                                             4387
```

<210> SEQ ID NO 3
<211> LENGTH: 36
<212> TYPE: PRT
<213> ORGANISM: Homo sapiens

<400> SEQUENCE: 3

```
Ile Lys Ala Ala Ile Gly Glu Arg Lys Gln Thr Phe Glu Asp Tyr Leu
 1               5                  10                  15

Glu Glu Gln Ile Gln Leu Glu Glu Gln Glu Leu Lys Gln Lys Gln Leu
             20                  25                  30

Lys Glu Ala Glu
         35
```

METHODS AND COMPOSITIONS FOR DESTABILIZING MICROTUBULES

FIELD OF THE INVENTION

The following invention relates to polypeptides that possess microtubule-destabilizing activity, polynucleotides encoding such polypeptides, and compositions and methods of use thereof.

References

The following publications are cited in this application:

Belmont, L. D. and Mitchison, T. J. (1996) Identification of a protein that interacts with tubulin dimers and increases the catastrophe rate of microtubules. *Cell*, 84, 623–631.

Cassimeris, L. and Spittle, C. (2001) Regulation of microtubule-associated proteins. *Int Rev Cytol*, 210, 163–226.

Cassimeris, L. (2002) The oncoprotein 18/stathmin family of microtubule destabilizers. *Curr Opin Cell Biol*, 14, 18–24.

Conboy, J. G., Chan, J., Mohandas, N. and Kan, Y. W. (1988) Multiple protein 4.1 isoforms produced by alternative splicing in human erythroid cells. *Proc Natl Acad Sci U S A*, 85, 9062–9065.

Conboy, J. G., Chan, J. Y., Chasis, J. A., Kan, Y. W. and Mohandas, N. (1991) Tissue- and development-specific alternative RNA splicing regulates expression of multiple isoforms of erythroid membrane protein 4.1. *J Biol Chem*, 266, 8273–8280.

De Carcer, G., Lallena, M. J. and Correas, I. (1995) Protein 4.1 is a component of the nuclear matrix of mammalian cells. *Biochem J*, 312 (Pt 3), 871–877.

Desai, A., Verma, S., Mitchison, T. J. and Walczak, C. E. (1999) Kin I kinesins are microtubule-destabilizing enzymes. *Cell*, 96, 69–78.

Erickson, H. P. and Stoffler, D. (1996) Protofilaments and rings, two conformations of the tubulin family conserved from bacterial FtsZ to alpha/beta and gamma tubulin. *J Cell Biol*, 135, 5–8.

Fields, B. N. ed. (1996) *Fields Virology*. Lippincott-Raven. Philadelphia, Pa., U.S.A.

Gennaro, A. R. ed. (2000) *Remington's Pharmaceutical Sciences*, 20th edition. Williams & Wilkins PA, U.S.A.

Hartman, J. J., Mahr, J., McNally, K., Okawa, K., Iwamatsu, A., Thomas, S., Cheesman, S., Heuser, J., Vale, R. D. and McNally, F. J. (1998) Katanin, a microtubule-severing protein, is a novel AAA ATPase that targets to the centrosome using a WD40-containing subunit. *Cell*, 93, 277–287.

Harlow, E. and Lane, D. (1988) *Antibodies: A laboratory manual*. Cold Spring Harbor Laboratory Press.

Heald, R. and Nogales, E. (2002) Microtubule dynamics. *J Cell Sci*, 115, 3–4.

Huang, J. P., Tang, C. J., Kou, G. H., Marchesi, V. T., Benz, E. J., Jr. and Tang, T. K. (1993) Genomic structure of the locus encoding protein 4.1. Structural basis for complex combinational patterns of tissue-specific alternative RNA splicing. *J Biol Chem*, 268, 3758–3766.

Hung, L. Y., Tang, C. J. and Tang, T. K. (2000) Protein 4.1 R-135 interacts with a novel centrosomal protein (CPAP) which is associated with the gamma-tubulin complex. *Mol Cell Biol*, 20, 7813–7825.

Krauss, S. W., Larabell, C. A., Lockett, S., Gascard, P., Penman, S., Mohandas, N. and Chasis, J. A. (1997) Structural protein 4.1 in the nucleus, of human cells: dynamic rearrangements during cell division. *J Cell Biol*, 137, 275–289.

Krauss, S. W., Chasis, J. A., Rogers, C., Mohandas, N., Krockmalnic, G. and Penman, S. (1997) Structural protein 4.1 is located in mammalian centrosomes. *Proc Natl Acad Sci U S A*, 94, 7297–7302.

Mattagajasingh, S. N., Huang, S. C., Hartenstein, J. S., Snyder, M., Marchesi, V. T. and Benz, E. J. (1999) A nonerythroid isoform of protein 4.1R interacts with the nuclear mitotic apparatus (NuMA) protein. *J Cell Biol*, 145, 29–43.

McCabe, P. M., Pfeiffer, P., Van Alfen, N. K. (1999) The influence of dsRNA viruses on the biology of plant pathogenic fungi. *Trends Microbiol*, 7:377–81.

McNally, F. J. and Vale, R. D. (1993) Identification of katanin, an ATPase that severs and disassembles stable microtubules. *Cell*, 75, 419–429.

Peng, B., Sutherland, K. D., Sum, E. Y., Olayioye, M., Wittlin, S., Tang, T. K., Lindeman, G. J. and Visvader, J. E. (2002) CPAP is a novel stat5-interacting cofactor that augments stat5-mediated transcriptional activity. *Mol Endocrinol*, 16, 2019–2033.

Perez-Ferreiro, C. M., Luque, C. M. and Correas, I. (2001) 4.1R proteins associate with interphase microtubules in human T cells: a 4.1R constitutive region is involved in tubulin binding. *J Biol Chem*, 276, 44785–44791.

Rao, J. S. (2003) Molecular mechanisms of glioma invasiveness: the role of proteases. *Nat Rev Cancer*, 3:489–501.

Rochefort, H., Capony, F., Garcia, M (1990) Cathepsin D in breast cancer: from molecular and cellular biology to clinical applications. *Cancer Cells*, 2:383–88.

Schiebel, E. (2000) gamma-tubulin complexes: binding to the centrosome, regulation and microtubule nucleation. *Curr Opin Cell Biol*, 12, 113–118.

Tang, T. K., Leto, T. L., Correas, I., Alonso, M. A., Marchesi, V. T. and Benz, E. J., Jr. (1988) Selective expression of an erythroid-specific isoform of protein 4.1. *Proc Natl Acad Sci U S A*, 85, 3713–3717.

Tang, T. K., Qin, Z., Leto, T., Marchesi, V. T. and Benz, E. J., Jr. (1990) Heterogeneity of mRNA and protein products arising from the protein 4.1 gene in erythroid and nonerythroid tissues. *J Cell Biol*, 110, 617–624.

Todd, S., Anderson, C., Jolly, D. J., Craik, C. S. (2000) HIV protease as a target for retrovirus vector-mediated gene therapy. *Biochim Biophys Acta.*, 1477(1–2):168–188.

Walczak, C. E., Mitchison, T. J. and Desai, A. (1996) XKCM1: a Xenopus kinesin-related protein that regulates microtubule dynamics during mitotic spindle assembly. *Cell*, 84, 37–47.

Zheng, Y., Wong, M. L., Alberts, B. and Mitchison, T. (1995) Nucleation of microtubule assembly by a gamma-tubulin-containing ring complex. *Nature*, 378, 578–583.

All of the publications cited above or elsewhere in this application are herein incorporated by reference in their entirety to the same extent as if the disclosure of each individual publication was specifically and individually indicated to be incorporated by reference in its entirety.

BACKGROUND OF THE INVENTION

Microtubules are essential for a variety of cellular functions, including maintenance of cell shape, cell movement, cell polarity, intracellular transport, mitosis, and meiosis. Microtubule networks exist in dynamic equilibrium and undergo dramatic reorganization through the course of the cell cycle. For example, upon entering mitosis, the interphase microtubule network is rapidly disassembled, followed by the reorganization of microtubules into the mitotic spindle.

Microtubules are comprised of α-β tubulin heterodimers, which are commonly assembled and nucleated by the γ-tubulin protein complexes resided in the centrosomes (Zheng et al., 1995; Erickson and Stoffler, 1996). Regulation of microtubule formation is controlled by two groups of proteins, namely microtubule stabilizers and destabilizers (Heald and Nogales, 2002). The former group is exemplified by microtubule-associated proteins (MAPs), which bind to and stabilize microtubules (Cassimeris and Spittle, 2001). The latter group includes Op18/stathmin (Belmont and Mitchison, 1996; Cassimeris, 2002), katanin (McNally and Vale, 1993; Hartman et al., 1998), and Kin I kinesins (Walczak et al., 1996; Desai et al., 1999), which possess the ability to disassemble microtubules.

Protein 4.1R, originally identified as an 80-kDa protein (i.e., 4.1R-80) in human erythrocytes, plays a crucial role in maintaining the specialized mechanical properties of erythrocyte plasma membranes. Multiple protein 4.1R isoforms, generated-by alternative RNA splicing, have been identified in erythroid (Tang et al., 1988; Conboy et al., 1988) and nonerythroid (Tang et al., 1990; Conboy et al., 1991; Huang et al., 1993) cells.

In addition to being associated with the plasma membrane cytoskeleton, protein 4.1R also localizes to intracellular sites in nucleated cells, including the nuclear matrix (De Career et al., 1995; Krauss et al., 1997a), microtubules (Perez-Ferreiro et al., 2001), and centrosomes (Krauss et al., 1997b; Hung et al., 2000). A nonerythroid isoform of 4.1R (4.1R-135) has also been reported to interact with the nuclear mitotic apparatus protein (NuMA) in the interphase nucleus, forming a complex with several spindle-pole organizing proteins, including NuMA, dynein, and dynactin, during cell division (Mattagajasingh et al., 1999). The 4.1R-135 isoform is generated by alternative mRNA splicing, which produces a mRNA encoding a polypeptide having an additional 209 N-terminal amino acid residues, relative to the erythroid 4.1R-80 isoform (Tang et al., 1990). The subcellular localization and the interaction of the nonerythroid 4.1R-135 isoform with NuMA suggest an essential role of 4.1R-135 in organizing the architecture of the nucleus and mitotic spindle (Mattagajasingh et al., 1999).

Using the N-terminal head region of 4.1R-135 (i.e., amino acid residues 1–209) in a yeast two-hybrid screening assay, a centrosomal protein designated centrosomal P4.1-associated protein (CPAP) was identified (Hung et al., 2000). In addition to binding to the head region of 4.1R-135, CPAP is associated with the γ-tubulin complex. Although increasing numbers of factors have been identified that are important for microtubule functions, their mode of action and practical use are yet to be elucidated.

SUMMARY OF THE INVENTION

The invention provides polypeptides, and polynucleotides encoding such polypeptides, that are useful for destabilizing microtubules. Since microtubules play an essential role in cell division, which occurs more frequently in tumor cells, the polypeptides and polynucleotides of the present invention can be used to treat tumors.

Accordingly, one aspect of the invention provides an isolated polypeptide selected from the group consisting of:
  a) a polypeptide of amino acid residues 311–422 of SEQ ID NO:1 (FIG. 6; GenBank AAG21074; Hung et al., 2000); and
  b) a polypeptide that shares substantial sequence similarity with residues 311–422 of SEQ ID NO:1 and has microtubule destabilizing activity.

In one embodiment of the invention, the polypeptide is a recombinant polypeptide, for example, a fusion polypeptide comprising amino acid residues 311–422 of SEQ ID NO:1, or a polypeptide that shares substantial sequence similarity thereto and has microtubule destabilizing activity. The recombinant polypeptide may comprise additional flanking or internal polypeptide sequences that modulate expression, solubility, activity, specificity, localization, or stability, or that facilitate purification or identification.

The polypeptide may be synthetic, and comprise artificial or modified amino acid residues. The synthetic polypeptide may also comprise additional amino acid residues that modulate solubility, activity, specificity, localization, or stability, or that facilitate synthesis, purification or identification.

In another embodiment, the invention provides a polynucleotide encoding the polypeptide described above. In one particular embodiment of the invention, the polynucleotide comprises nucleotide 1141 to nucleotide 1476 of SEQ ID NO:2 (FIG. 7; GenBank AF139625; Hung et al., 2000).

In one embodiment, the invention provides a method for destabilizing microtubules in a cell, comprising providing to the cell a polypeptide in a sufficient amount to destabilize microtubules in the cell, wherein the polypeptide is selected from the group consisting of:
  a) a polypeptide of amino acid residues 311–422 of SEQ ID NO:1;
  b) a polypeptide that shares substantial sequence similarity with residues 311–422 of SEQ ID NO:1 and has microtubule destabilizing activity,
  c) a polypeptide of SEQ ID NO:1; and
  d) a polypeptide that shares substantial sequence similarity with SEQ ID NO:1 and has microtubule destabilizing activity.

In a further embodiment, the invention provides a method for inhibiting proliferation of a cell, comprising providing to the cell a polypeptide of the present invention in a sufficient amount to inhibit proliferation of the cell.

In yet another embodiment of the invention, the invention provides a method for treating a tumor, comprising providing to cells of the tumor a polypeptide of the present invention in a sufficient amount to inhibit proliferation of the cell.

The polypeptide can be provided as a polynucleotide that encodes the polypeptide, such as an expression vector. In one embodiment of the invention, the polypeptide is expressed using an inducible promoter.

In one embodiment of the invention, the expression vector specifically or preferentially replicates in the cells in which microtubule destabilization is desired, particularly tumor cells. The vector is preferably derived from a virus, for example, a virus selected from the group consisting of retroviruses, adenoviruses, adeno-associated viruses, pox viruses, or herpesviruses. In a particular embodiment of the invention, the vector is derived from a lentivirus.

In still another embodiment, the invention provides a method for screening drugs that modulate microtubule assembly, comprising contacting microtubules with a polypeptide of the present invention, in the presence and absence of a drug, and determining the effect of the drug on microtubule assembly. The polypeptide may be any PN2-3 polypeptide, or a compound comprising a PN2-3 polypeptide. In a particular embodiment of the invention, such drugs modulate microtubule assembly by modulating PN2-3.

In yet another embodiment of the invention, the above-described polypeptides, or polynucleotides encoding such polypeptides, are provided to cells in the presence of one or more drugs that affect microtubule assembly or stability. For example, the polypeptides of the invention can be used to destabilize taxol-stabilized microtubules, such as would be found in a mammal receiving taxol to reduce the risk of restenosis following stent implantation.

BRIEF DESCRIPTION OF THE DRAWINGS

FIG. 5 shows the results of flow cytometry analysis of cells transfected with GFP or GFP-PN2-3 expression vectors. The horizontal and vertical axes represent relative DNA content and cell number, respectively.

FIG. 6 shows the amino acid sequence of CPAP (SEQ ID NO:1). Amino acids 311–422 are underlined.

FIG. 7 shows the cDNA sequence that codes for CPAP (SEQ ID NO:2). Nucleotides 1141–1476 are underlined.

DETAILED DESCRIPTION OF THE INVENTION

Figure 1:
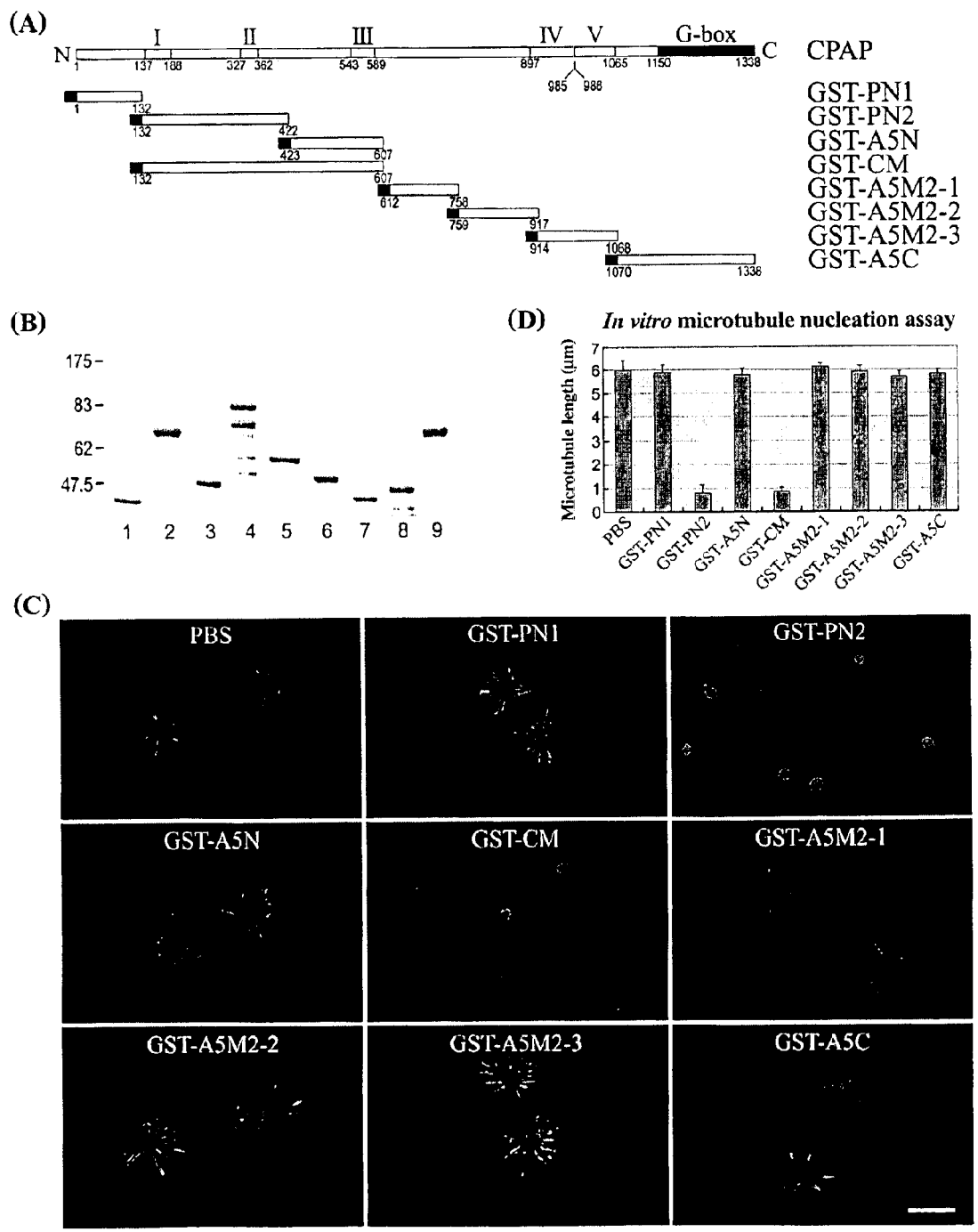
FIG. 1 shows inhibition of microtubule nucleation from purified centrosomes by polypeptides derived from CPAP. (A) Diagram depicting cDNA constructs encoding various portions of CPAP. (B) Coomassie-stained polyacrylamide gel showing affinity-purified GST-truncated CPAP fusion proteins. (C) Results of an in vitro microtubule nucleation assay showing the effect of truncated CPAP fusion proteins on microtubule nucleation. (D) Quantitative analysis of the inhibitory effects observed in (C).

Prior to describing the invention in further detail, the terms used in this description are defined as follows unless otherwise indicated.

Definitions

Administering (to cells): Delivering the object of the invention to a target population of cells. As used herein, administering encompasses any methodology, route of delivery, and technique useful for bringing the polypeptides and/or polynucleotides of the invention into contact with the target population of cells, including but not limited to, infection, transfection, transduction, ballistic delivery, microinjection, and any form of receptor or carrier-mediated transport.

Depolymerizing (depolymerization of) microtubules: Depolymerizing (depolymerization of) microtubules: The process of disassembling microtubules into their component subunits (usually α-β heterodimers).

Domain: As used herein, domains of polypeptides are regions that possess a characteristic structure or function. Examples of domains include α-helices, β-sheets, β-bends, loops, and unstructured polypeptide regions between structured regions.

Expressing a polypeptide in the target cells: Causing target cells to produce, via protein translation, a polypeptide sequence of interest (e.g., CPAP or a portion thereof) from a polynucleotide encoding such polypeptide.

Expression vector: A vector that encodes one or more polypeptides of interest along with appropriate transcriptional and translational regulatory sequences to allow expression of the polypeptide in a cell. Examples of expression vectors include plasmids, phages, and viruses. Expression vectors may comprise inducible or cell-type-specific promoters, enhancers or repressors, introns, polyadenylation signals, selectable markers, polylinkers, site-specific recombination sequences, and other features to improve functionality, convenience of use, and control over mRNA and/or protein expression levels, as known in the art.

Fusion protein: A contiguous polypeptide comprising polypeptide sequences derived from a plurality of sources.

Inducible promoter: A promoter that causes RNA to be transcribed from a particular polynucleotide sequence at different levels depending upon specific intracellular or environmental conditions. Inducible promoters may respond positively or negatively to, for example, the presence of hormones, nutrients, metabolites, toxins, stress, osmolarity, the activation or inactivation of certain cellular biochemical pathways, or other means of regulating gene expression.

Inhibiting proliferation of a cell (inhibits proliferation): Decreasing the number of mitotic divisions of a cell within a given amount of time. Inhibition may be partial, such that the cell continues to undergo mitotic division but at a decreased rate compared to a similar cell in a comparable environment, or complete, such that the cell ceases to undergo mitotic division.

Microtubule destabilizing activity: The activity of preventing, inhibiting, or reversing the polymerization of microtubules. Thus, a microtubule destabilizing activity may be the activity to inhibit microtubule nucleation or depolymerize existing microtubule either in vitro or in vivo.

Modulate microtubule assembly: To cause disassembly or assembly of microtubules or to shift the dynamic equilibrium of microtubule formation so as to favor the formation of free tubulin or microtubule.

Naturally occurring variant: A polynucleotide or polypeptide sequence that is found in nature and that possesses a high degree of structural and functional identity to a subject polynucleotide or polypeptide. Naturally occurring variants include but are not limited to polynucleotides or polypeptides having different transcriptional or translation start and/or stop positions, respectively; splice variants; variants resulting from gene rearrangement, duplication, inversion, deletion, and/or recombination; allelic variants; variants resulting from RNA editing; and other events know to alter polynucleotide and/or polypeptide sequences. Preferably, such variants have at least 98%, at least 95%, or at least 90% polypeptide sequence identity with respect to a particular polynucleotide or polypeptide sequence of interest.

PN2-3 activity: A biological activity of PN2-3 disclosed herein, such as the microtubule destabilizing activity, proliferation-inhibiting activity, or cell cycle arrest activity. Microtubule destabilizing activity can be determined by any method known in the art, preferably one of the assays described or referenced herein.

PN2-3 polypeptide: A polypeptide having substantial sequence similarity with residues 311–422 of CPAP (SEQ ID NO:1) and having at least one PN2-3 activity. The polypeptide preferably has a helical region and a non-helical region as predicted by any software available in the art. A PN2-3 polypeptide in which the helical and non-helical regions are switched, yet retaining at least one PN2-3 activity, is also contemplated herein.

PN2-3 sequence or PN2-3 region: Amino acid sequence of residues 311–422 of CPAP (SEQ ID NO:1).

Polypeptide: A molecule having any number of contiguous amino acid residues linked via peptide bonds. As used herein, polypeptide, peptide, and protein are interchangeable.

Providing to the cell: Bringing into contact with a cell or causing to be taken up by a cell.

Substantial sequence similarity: With respect to polypeptides, substantial sequence similarity exists when two polypeptide sequences are at least about 50%, at least about 60%, at least about 70%, at least about 80%, at least about 90%, or at least about 95% identical at the primary sequence level, as determined by a sequence alignment program available in the art, such as Clustal W.

Sufficient amount: An amount that is effective in achieving an intended result or obtaining a desired effect.

Taxol-stabilized microtubules: Microtubules that are resistant to depolymerization due to the presence of taxol.

Treating or ameliorating a disease or medical condition: reducing or completely removing the symptoms of a disease or medical condition.

Tumor cells, also known as neoplastic cells: Cells which proliferate without the normal growth inhibition properties. A new growth comprising neoplastic cells is a neoplasm or tumor. A neoplasm is an abnormal tissue growth, generally forming a distinct mass, that grows by cellular proliferation more rapidly than normal tissue growth. Neoplasms may show partial or total lack of structural organization and functional coordination with normal tissue. As used herein, a neoplasm is intended to encompass hematopoietic neoplasms as well as solid neoplasms.

A neoplasm may be benign (benign tumor) or malignant (malignant tumor or cancer). Malignant tumors can be broadly classified into three major types. Malignant neoplasms arising from epithelial structures are called carcinomas, malignant neoplasms that originate from connective tissues such as muscle, cartilage, fat or bone are called sarcomas and malignant tumors affecting hematopoietic structures (structures pertaining to the formation of blood cells) including components of the immune system, are called leukemias and lymphomas. Other neoplasms include, but are not limited to neurofibromatosis.

A disease or medical condition of which the symptoms include a tumor may also be referred to as a tumor or neoplasm.

DETAILED DESCRIPTION OF THE INVENTION

The invention provides a 112-amino acid residue polypeptide derived from centrosomal P4.1-associated protein (CPAP; SEQ ID NO:1) that possesses the ability to inhibit microtubule formation. The polypeptide contains residues 311–422 of CPAP. The invention further provides polynucleotides encoding such polypeptides, and compositions and methods of use thereof.

The polypeptide was discovered as a result of a structure-function analysis of CPAP. Briefly, an in vitro microtubule nucleation assay was developed to determine whether the CPAP polypeptide comprised a functional portion that affected microtubule assembly nucleated from a centrosome. As described in Example 1, polynucleotide sequences encoding truncated forms of the CPAP polypeptide were cloned into a glutathione-S-transferase (GST)-expression vector, PGEX-2T, for expression of GST-truncated CPAP polypeptides. These GST-truncated CPAP proteins were then tested for their ability to affect microtubule formation. The results indicate that PN2, residues 132–422 of CPAP, inhibited microtubule formation.

To more precisely define the region of PN2 that was responsible for inhibiting microtubule nucleation, expression vectors were constructed to express GST-fusion polypeptides comprising one of three sub-regions of PN2. Only GST-PN2-3 (corresponding to residues 311–422 of CPAP) possessed the ability to inhibit microtubule assembly, indicating that the portion of PN2 necessary to inhibit centrosome-dependent microtubule nucleation resides in the PN2-3 region.

Figure 3:
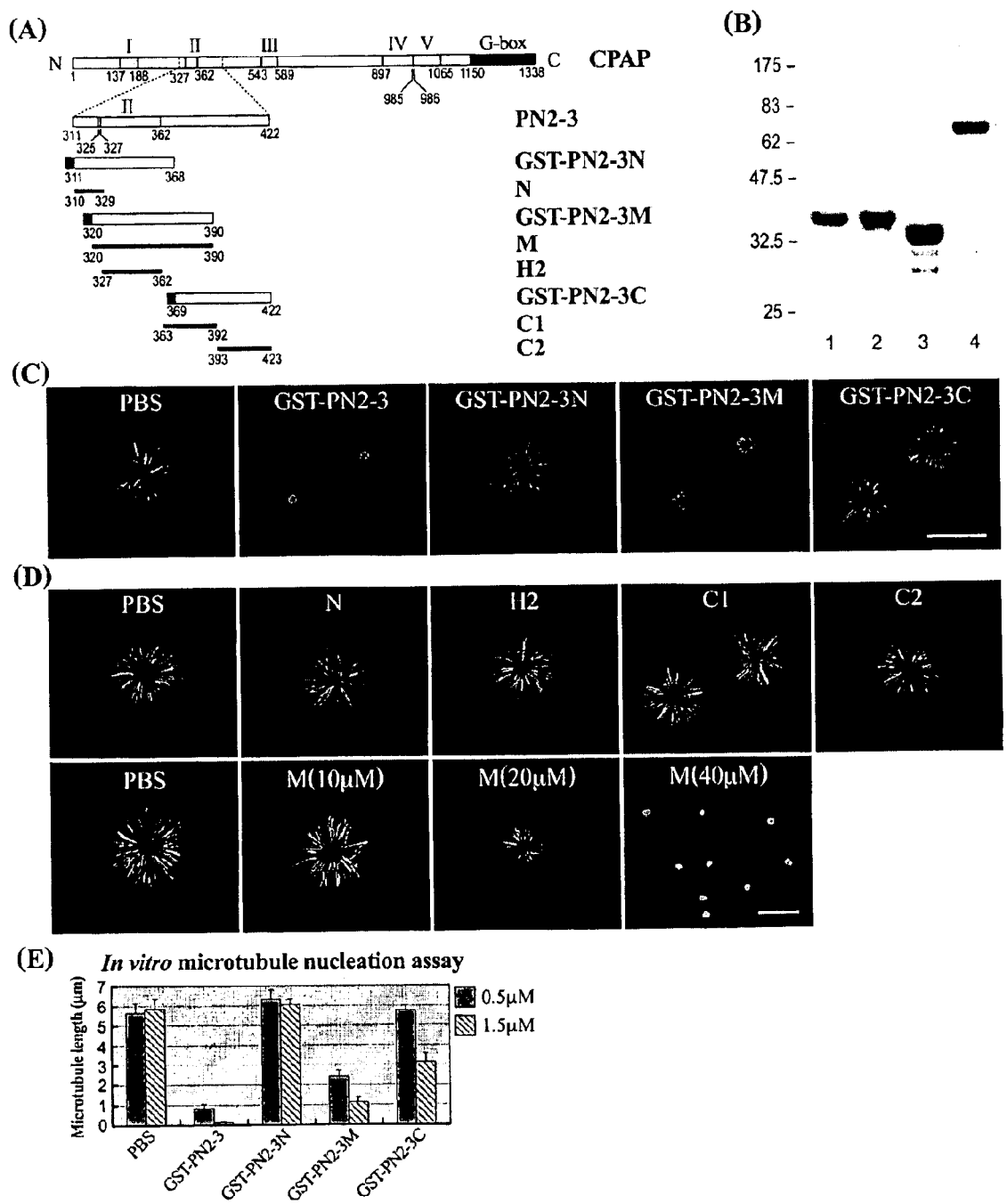
FIG. 3 shows inhibition of microtubule nucleation by portions of the PN2-3 fragment of CPAP. (A) Diagram depicting cDNA constructs and synthetic peptides encoding various portions of the PN2-3 fragment of CPAP. (B) Coomassie-stained polyacrylamide gel showing affinity-purified GST-truncated PN2-3 CPAP fusion proteins. (C and D) Results of an in vitro microtubule nucleation assay showing the effect of truncated PN2-3 CPAP fusion proteins (C) and the synthetic peptide derived from PN2-3 (D) on microtubule nucleation. (E) Quantitative analysis of the inhibitory effects observed in (C). (F) Location of the proline substitutions in four mutated PN2-3 polypeptides and the predicted relative probability (compared to the wild-type sequence (i.e., SEQ ID NO: 3)) that each mutated polypeptide will form an α-helical domain. (G) Results of an in vitro microtubule nucleation assay using the polypeptides of (F) along with wild-type PN2-3.
Figure 3:
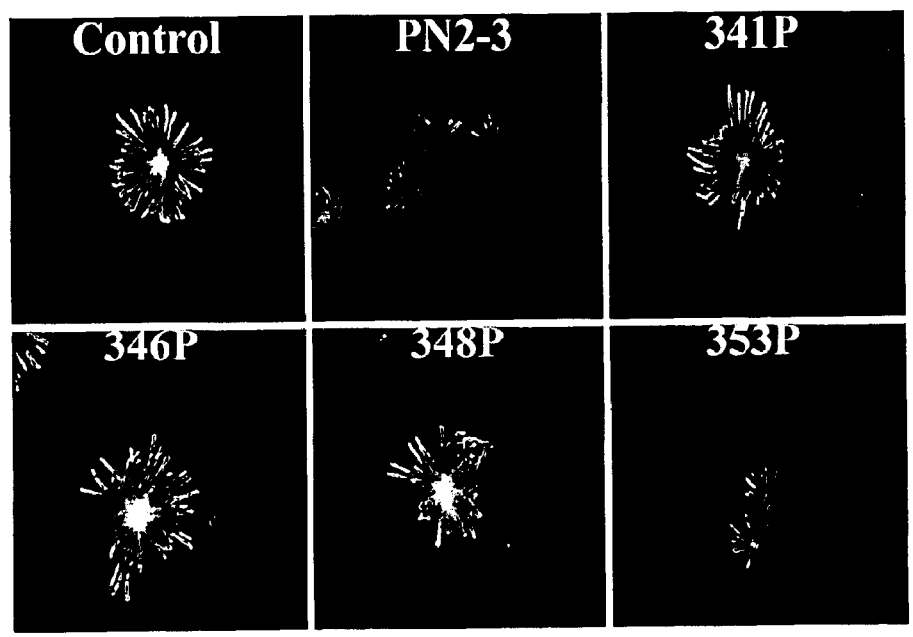

The CPAP polypeptide comprises five α-helical coiled-coil motifs, designated I to V, which are punctuated by a helix-disrupting proline residue (Hung et al., 2000; FIG. 3A). The PN2-3 region of CPAP comprises both an α-helical domain (residues 327–362) and a non-helical structure (residues 363–422). To examine the role of this α-helical structure, the PN2-3 polypeptide was further divided into three sub-regions that comprised the α-helical motif (PN2-3N), the non-helical motif (PN2-3C), or both (PN2-3M). The polypeptides inhibited microtubule nucleation with the following relative level of efficacy: GST-PN2-3>GST-PN2-3M>GST-PN2-3C. No inhibition was observed in the case of GST-PN2-3N, which comprises only the α-helical motif. Accordingly, both the α-helical and the non-helical structures in PN2-3 are required for the most effective inhibition of microtubule nucleation from the centrosomes.

To further define the amino acid residues and/or polypeptide secondary structures responsible PN2-3 activity, four residues within the putative amino acid sequence of α-helix domain II (residues 327–362) were mutated to the known helix-disrupting residue, proline. Thus, Y341, I346, L348, and L353 were individually mutated to proline. In the microtubule nucleation assay, only the wild-type and L353P polypeptides inhibited microtubule assembly. Therefore, the amino acid residues at positions 341, 346, and 348 (but not 353) are important for PN2-3 activity, presumably due to their structural role in forming or maintaining α-helical domain II.

By expressing PN2-3 or its related polypeptides in cultured cells, it was further discovered that the polypeptides inhibit cell proliferation and cause $G_2/M$ arrest in the cell cycle. Therefore, the polypeptides can be used to inhibit microtubule formation and cell proliferation.

Accordingly, the present invention provides a polypeptide that is derived from CPAP and possesses the ability to sequester or disassemble microtubules. The most active polypeptide (PN2-3) was a 112-amino acid residues in length and comprised both a predicted α-helical structure (residues 327–362) and non-helical structure (residues 363–422) of CPAP. No significant sequence homology was found between PN2-3 and other known microtubule destabilizing polypeptides, including OP18/stathmin (Belmont and Mitchison, 1996; Cassimeris, 2002), katanin (McNally and Vale, 1993; Hartman et al., 1998), and Kin I kinesins (Walczak et al., 1996; Desai et al., 1999). Therefore, the PN2-3 polypeptide represents a novel type of microtubule destabilizing sequence.

Without being limited to a theory, it is believed that the PN2-3 polypeptide directly recognizes the "plus ends" of microtubules, which results in the inhibition of microtubule nucleation from centrosomes. This mechanism is supported by the observation that GST-PN2-3 and GST-CM localize to the plus ends of newly assembled microtubules, formed in the presence of centrosomes (data not shown). However, in the absence of centrosomes, the PN2-3 polypeptide also destabilizes microtubules, suggesting that the PN2-3 polypeptide may bind to tubulin subunits, causing the disassembly of existing microtubules. The ability of the PN2-3 polypeptide to both inhibit microtubule nucleation from centrosomes and cause the disassembly of microtubules make PN2-3 particularly effective as a substance for modulating microtubule assembly in cells, including but not limited to rapidly proliferating cells, such as cancer cells.

Accordingly, in one embodiment, the instant invention provides the 112-amino acid residue-PN2-3 polypeptide, which comprises amino acid residues 311–422 of CPAP (SEQ ID NO:1). The PN2-3 polypeptide possesses the ability to inhibit microtubule formation in various assays, including inhibiting the formation of microtubule nucleated from centrosomes and destabilize polymerized tubulin. Also provided are PN2-3 polypeptides that have substantial sequence similarity with amino acid residues 311–422 of CPAP, as well as a PN2-3 activity. PN2-3 activity can be determined, for example, by using any of the biological assays described herein. A PN2-3 polypeptide has preferably about 50–500 amino acids, more preferably about 75–400 amino acids, yet more preferably about 100–300 amino acids, still more preferably about 100–250 amino acids, and most preferably about 100–200 amino acids.

Such polypeptides may be derived from naturally-occurring variants of CPAP or may be engineered polypeptides. In a preferred embodiment of the invention, such polypeptides comprise conservative amino acid substitutions, which are well known to those skilled in the art. Conservative amino acid substitutions include but are not limited to the substitution of amino acids with residues of similar charges, sizes, and/or hydrophobic and hydrophilic characteristics.

One embodiment of the invention provides a polypeptide comprising the PN2-3 sequences in the context of a larger polypeptide, including but not limited to the full-length CPAP polypeptide or portions thereof, provided that the resulting polypeptides demonstrate PN2-3 activity. A particular embodiment of the invention provides the CM polypeptide (comprising amino acid residues 132–607 of CPAP). Another embodiment of the invention provides the PN2 polypeptide (comprising amino acid residues 132–422 of CPAP).

Yet another embodiment of the invention includes a portion of the PN2-3 polypeptide, provided that the portion of the PN2-3 polypeptide demonstrates PN2-3 activity. In one embodiment of the invention, the portion of PN2-3 is PN2-3M, which comprises amino acid residues 320–390 of CPAP. Other portions of PN2-3 may also retain PN2-3 activity. For example, PN2-3C, which comprises amino acid residues 369–422 of CPAP, is known to retain some PN2-3 activity, although it is less active than PN2-3M. Additional polypeptides of the invention may be identified by expressing or synthesizing different portions of the PN2-3 region and assaying the polypeptides for PN-2-3 activity, using any of the methods described herein. Other methods available in the art for determining microtubule destabilizing activities can also be employed.

The invention also provides a fusion polypeptide comprising a PN2-3 polypeptide along with additional amino acid sequences. These additional sequences may facilitate expression, purification, identification, solubility, membrane transport, stability, activity, localization, toxicity, or specificity of the resulting polypeptide.

In one embodiment of the invention, the additional amino acid sequences encode a portion of glutathione-S-transferase (GST), which allows affinity purification of the fusion polypeptide. In a particular embodiment of the invention, a protease cleavage site is provided between the GST sequence and CPAP sequence that comprises the PN2-3 sequences, such that the GST sequences may be removed by a protease that recognizes the cleavage site. Proteases and cognate recognition sequences that are useful for practicing the invention include, but are not limited to, thrombin or Factor VIII. Virtually any affinity tag may be expressed as part of the fusion polypeptide, provided that it does not cause irreversible misfolding and degradation of the fusion polypeptide. Similarly, virtually any protease is useful for cleaving an affinity tag when a cognate recognition sequence is provided between the tag and the PN2-3 sequence, so long as the protease does not affect PN2-3 activity, for example, by cleaving the PN2-3 polypeptide internally.

In a related embodiment of the invention, the additional amino acid sequences may provide a mechanism for modulating the activity of the expressed polypeptide such that the PN2-3 activity is only present in particular types of cells (i.e., target cells). In one embodiment, the additional sequences may resemble the plus ends of microtubules or tubulin subunits, such that the PN2-3 polypeptide of the fusion protein binds to the "decoy" sequence, thereby preventing or inhibiting the PN2-3 polypeptide from interacting with cellular microtubules. In a most preferred embodiment of the invention, such a fusion protein would further comprise a protease cleavage site between the PN2-3 polypeptide and the decoy portion of the fusion protein. The decoy portion could then be removed by a protease present specifically, or predominantly, in the target cells.

In a preferred embodiment of the invention, such a protease could be endogenous to the target cells. For example, the protease cathepsin D is known to be overexpressed in breast cancer cells, and is believed to be responsible for increased invasiveness (Rochefort, 1990). Urokinase-type plasminogen activator (uPA), cathepsin B, and matrix metalloproteinases MMP2 and MMP9 are known to be present at increased levels in high-grade astrocytomas, relative to levels in normal cells or low-grade astrocytomas, and are believed to degrade the extracellular matrix (ECM) (Rao, 2003). A protease known to be overexpressed by certain cancer cells, or known to be over-expressed at sites of metastatic invasion, could be used to activate (i.e., cleave the region responsible for modulating the activity of) the PN2-3 polypeptide, specifically or preferentially in the target cells. Such an arrangement provides precise control over PN2-3 activity and allow the selective killing of target cells, particularly cancer cells.

In an alternative embodiment of the invention, an additional expression vector is provided to the mixed population of cells, wherein the additional expression vector encodes a protease under the control of a promoter that is specifically or preferentially active in the target cells. Such a promoter could be selected by identifying proteins that are overexpressed in a target cell type and using a promoter from a gene encoding such proteins to control expression of the protease. Accordingly, a polypeptide having PN2-3 activity would only be generated in cells that expressed the protease.

The additional sequences may also be used to target delivery of the fusion polypeptide. For example, the additional sequences may correspond to a polypeptide ligand specific for a receptor or surface molecule that is differentially-expressed, presented, or modulated in target cells. Any such additional sequences may be used, provided that the presence of the PN2-3 region does not abolish the ability of the cell-type specific portion of the fusion polypeptide to be recognized and internalized by a cell possessing the appropriate cell surface molecules and that the additional sequences do not interfere with PN2-3 activity. Optionally, the cell-type specific portion of the polypeptide may be cleaved by a protease, as described above.

Polypeptides comprising other amino acid substitutions, deletions, or insertions, with respect to the PN2-3 region, may also be useful for practicing the invention provided that they retain PN2-3 activity and/or specificity. As discussed above, substitutions that disrupt α-helical domain II (e.g., Y341P, I346P, and L348P) appear to reduce or abolish PN2-3 activity, while the L353 substitution does not affect the activity. Polypeptides comprising non-naturally-occurring amino acids, non-amino acid moieties (including but not limited to, carbohydrate and lipid moieties) may also be useful for practicing the invention. Such polypeptides may be synthetic polypeptides and may include any number of non-naturally-occurring amino acids and/or additional functional groups (including but not limited to fluorescence and/or quenching groups), provided that the resulting polypeptides retain PN2-3 activity.

The invention also includes methods of using the polypeptides of the invention. In one embodiment, a PN2-3 polypeptide is administered to eukaryotic cells to destabilize microtubules in the cells, or prevent the assembly of microtubules. In a preferred embodiment of the invention, administration of the polypeptide decreases the rate of proliferation of such cells. In a particular embodiment of the invention, administration of the polypeptide prevents the cells from proliferating by causing $G_2/M$ arrest. In a most preferred embodiment of the invention, the cells are killed.

Numerous methods of introducing polypeptides into cells are known in the art, including but not limited to transfection, microinjection, scrape-loading, and receptor-mediated uptake by the cell. Transfection may be transient or stable. Exemplary current methods of transfection include, calcium phosphate precipitation, electroporation, lipofection, and peptide-mediated transfection. Ballistic DNA delivery and transduction (i.e., the introduction of foreign DNA by virus or virus vector infection) can also be employed.

For example, polypeptides of the present invention can be delivered to cells by means of an expression vector. Suitable expression vectors comprise a promoter that is active in the cells in which a PN2-3 polypeptide is to be expressed (i.e. target cells). For example, in the case of cancer cells, the promoter may be derived from a growth factor that is known to be overexpressed in the particular cancer cell. Alternatively, the promoter may be active during a certain stage of the cell cycle, such as the $G_2/M$ transition. In this manner, quiescent cells will not express the polypeptide comprising PN2-3 sequences, while cells entering the $G_2/M$ transition in the cell cycle will express such polypeptides. This feature of this particular embodiment of the invention may be desirable to prevent the expression of PN2-3 in nerve cells, which rely on extensive processes (involving elaborate microtubule architecture) for cell-cell communication. Since nerve cells are slow growing, and in some cases essentially quiescent (e.g., in the brain), promoters that are specific for the M or S phases of the cell cycle are unlikely to function in nerve cells.

Expression vectors useful for practicing the invention may also include selectable markers, cell-type or cell-cycle-specific enhancers or repressors, polylinkers, start codons, ribosome binding sites, internal ribosome entry sites, introns, stop codons, polyadenylation signals, or other features that facilitate cloning and vector stability, mRNA stability and localization in the cell, and translation efficiency, or combinations thereof. Expression vectors include viral expression vectors. Selection of these features is largely based on the target cells to which PN2-3 is to be delivered and the expression characteristics desired. A large number of commercially available vectors are available for expressing polypeptides in cells.

In one embodiment of the invention, the polynucleotides encoding the PN2-3 polypeptide are delivered to cells using a viral vector. Numerous viruses are known to be useful for delivering polynucleotides to animal cells (reviewed in Todd et al., 2000), including but not limited to adenoviruses, adeno-associated viruses, retroviruses (including lentiviruses), herpesviruses, and pox viruses. Plant viruses useful for delivering the polypeptides of the invention to plants include but are not limited to tobacco mosaic virus, cauliflower mosaic virus, alfalfa mosaic virus, and potato virus X. Fungal and protozoan species are also known to be susceptible to viral infection (Fields 1996 at pages 557–585; McCabe et al., 1999), providing a means to deliver polynucleotide sequences that encode a polypeptide comprising the PN2-3 to fungal or protozoan cells.

In one embodiment of the invention, the viral vector preferentially infects the target cells. In another embodiment of the invention, the viral vector preferentially replicates in the target cells, particularly rapidly dividing cells, such as cancer cells. Expression of PN2-3 in cells using a viral vector may also be modulated using a cell-type or cell-cycle-specific promoter, as well as other methods of regulating gene expression, described or referenced herein and known in the art.

The methods and compositions of the invention described herein may be combined with any other treatment or therapy for treating cancer, for example, chemotherapy, radiation therapy, surgery, and combinations thereof.

Because microtubules are ubiquitous in eukaryotic cells, the various embodiments of the invention described herein, and other embodiments that will become apparent to the skilled artisan based on the instant disclosure, can be applied to wide variety of different eukaryotic cells. The eukaryotic cells may be animal cells (including both protozoan species and multicellular animals), plant cells (including both algae and multicellular plants), or fungi. Such cells may exist in a multicellular organism, as endogenous cells, commensals, or parasites, or in culture.

In one embodiment of the invention, the target cells are tumor or neoplastic cells. The tumor cells may be metastatic. The tumor cells may be present in an animal or a plant. In a preferred embodiment, the animal is a non-human primate, canine, feline, bovine, ovine, porcine, or rodent. In another preferred embodiment, the animal is a human. The plant may be an economically important dicot or monocot, including but not limited to, fruit producing plants, grain crops, tubers, plants used to produce economically important medicines, herbs, recreation drugs, and variants and hybrids thereof. In particular embodiments of the invention, the plant is tobacco, corn, wheat, rice, barley, tomato, potato, or hybrids thereof.

In another embodiment of the invention, the target cells are mycotic (i.e., fungal) cells or protozoan cells, including but not limited to fungal or protozoan cells that infect immunocompromised and/or immunocompetent plants or animals. Examples of fungal cells that can be killed in the practice of the instant invention include but are not limited to *Candida, Coccidioides, Paracoccidioides, Cryptococcus, Histoplasma, Blastomyces, Rhinosporidium, Laboa, Entomophthora, Aspergillis, Rhodotolura, Trichosporon, Monosporium, Acremonium, Leptosphaeria, Geotrichum, Saccharomyces, Sporothrix, Exophilia, Madurella, Fusarium, Wangiella, Fonsecaea, Phialophora, Cladosporium, Tinea, Allescheria, Pseudoallescheria, Petriellidium, Epidemophyton, Pityrosporum, Mucor, Rhizopus, Absidia,* and *Cunninghamella* species. Additional examples include mushrooms and other edible fungi. Examples of protozoan cells that can be killed in the practice of the instant invention include but are not limited to *Pneumocystis, Giardia, Cryptosporidium, Entameoba, Endolimax, Iodameoba, Dientameoba, Toxoplasma, Malaria, Trichomonas, Balantidium,* and *Leishmania* species.

In another embodiment of the invention, the invention provides a method of screening drugs that modulate microtubule assembly or CPAP activity. In one embodiment, drug screening is performed by incubating a drug or test compound, along with a PN2-3 polypeptide, in an assay such as those described herein. In a particular embodiment of the invention, drugs are added to the assay in the presence or absence of PN2-3 polypeptides, and microtubule assembly is determined. In this manner, the practitioner can determine whether a drug inhibits or stimulates microtubule formation, and whether such inhibitory or stimulatory activity is dependent on the presence of a PN2-3 polypeptide. For example, if the drug modulates microtubule assembly only in the presence of a PN2-3 polypeptide, it is likely that the drug affects PN2-3 activity rather than modulating microtubule assembly directly. In this manner, the activity and mechanism of drugs that modulate microtubule formation may be determined.

The invention also provides antibodies that recognize a PN2-3 polypeptide. Methods of producing antibodies to polypeptides are well known in the art. Such methods have been described, for example, by Harlow and Lane (1988). Antibodies of the instant invention are useful, for example, for PN2-3 polypeptides within a cell to determine whether such polypeptides are associated with centrosomes. Antibodies specific for PN2-3 polypeptides can also be used to stain tissues of animals subject to the various embodiments of the invention to determine whether PN2-3 polypeptides are accumulating specifically or preferentially in the target cell type, thereby monitoring the in vivo localization of PN2-3 polypeptides.

The instant invention also includes pharmaceutical compositions, which contain, as an ingredient, one or more of the polypeptides and/or polynucleotides described herein. In one embodiment of the invention, the pharmaceutical composition comprises PN2-3 polypeptides. In another embodiment of the invention, the pharmaceutical composition comprises a polynucleotide encoding such a polypeptide. In preparing the pharmaceutical compositions of the invention, the polypeptides or polynucleotides are usually mixed with an excipient, diluted by an excipient, and/or enclosed within a carrier which can be in the form of a capsule, sachet, paper or other container. Any carriers or vehicles can be used that facilitate the administration of pharmacological agents, including the polynucleotides and polypeptides of the invention, to a target population of cells. Pharmaceutical compositions may also comprise appropriate immunosuppressants or immunostimulants.

When the pharmaceutically acceptable excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders. Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, sterile water, syrup, and methyl cellulose. Other suitable formulations for use in the present invention can be found in *Remington's Pharmaceutical Sciences*. In the case of the instant invention, sterile injectable solutions, for intratumoral or intravenous delivery, are the preferred pharmaceutical embodiments of the invention. Such pharmaceutical compositions may be packaged into convenient kits providing the necessary materials, instructions, and equipment. The pharmaceutical compositions can be administered in a single dose or in multiple doses through routes of inoculation and methods of delivery that are known in art.

The invention further provides kits that comprise at least one item selected from the group consisting of the following, particularly items 1–4:

1. a PN2-3 polypeptide, a polynucleotide encoding a PN2-3 polypeptide, and/or a composition comprising the polypeptide or polynucleotide;

2. an antibody recognizing the PN2-3 sequence;
3. a chemotherapeutic agent;
4. a means for delivering polypeptides or polynucleotides into a cell; and
5. an instruction of use.

While this invention has been particularly shown and described with references to preferred embodiments thereof, it will be understood by those skilled in the art that various changes in form and details may be made therein without departing from the spirit and scope of the invention as defined by the appended claims.

EXAMPLES

In the examples below, the following abbreviations have the following meanings. Abbreviations not defined have their generally accepted meanings:

| | |
|---|---|
| µg | microgram |
| µl | microliter |
| µM | micromolar |
| 2-ME | 2-mercaptoethanol (also called β-ME) |
| ATCC | American Type Culture Collection |
| ATP | adenosine 5'-triphosphate |
| CDNA | complimentary DNA |
| cm$^2$ | square centimeters |
| CMV | cytomegalovirus |
| CPAP | centrosomal P4.1-associated protein |
| CPE | cytopathic effects |
| DMEM | Dulbecco's modified Eagle's medium |
| DMSO | dimethylsulfoxide |
| DTT | dithiothrietol |
| EDTA | ethylenediaminetetraacetic acid |
| EGF | epidermal growth factor |
| EGFP-C1 | a green fluorescent protein plasmid |
| EGTA | ethyleneglycol-bis(β-aminoethylether)-N,N,N',N'-tetraacetic acid |
| FACS | fluorescent antibody cell sorting |
| FBS | fetal bovine serum |
| FITC | fluorosine isothiocyanate |
| FPLC | fast-protein liquid chromatography |
| g | gram (except "x g") |
| x g | times gravity |
| $G_0/G_1$ | growth phases between M and S |
| $G_2/M$ | growth phase-2/mitosis |
| GST | glutathione-S-transferase |
| GTP | guanosine 5'-triphosphate |
| HeLa | transformed human cervical carcinoma cells |
| HEPES | (N-[2-hydroxyethyl]piperazine-N'-[2-ethanesulfonic acid]) |
| hr | hour |
| L | liter |
| M | molar |
| MEM | Modified Eagle's medium |
| mg | milligram |
| min | minute |
| ml | milliliter |
| mM | millimolar |
| mm$^2$ | square millimeters |
| MOI | multiplicity of infection |
| n | number (e.g., number of animals or duplicates) |
| ° C. | degrees Celsius |
| PAGE | polyacrylamide gel electrophoresis |
| PBMC | primary blood mononuclear cells |
| PBS | phosphate buffered saline |
| PCR | polymerase chain reaction |
| PDGF | platelet derived growth factor |
| PFU | plaque forming units |
| PIPES | piperazine-N, N'-bis(2-ethanesulfonate) |
| PKR | double-stranded RNA activated protein kinase |
| rpm | revolutions per minute |
| RPMI | commonly-used cell culture medium |
| S | DNA synthesis phase |
| SDS | sodium dodecyl sulfate |
| SDS-PAGE | sodium dodecyl sulfate polyacrylamide gel electrophoresis |
| Tris-HCl | (hydroxymethyl)aminomethane hydrochloride |
| U | unit |
| UV | ultraviolet |

Materials and Methods

Plasmid Construction, Purification of GST-recombinant Proteins, and Peptide Synthesis cDNAs encoding different portions of CPAP were fused in-frame to glutathione-S-transferase (GST) using the plasmid PGEX-2T (Amersham, Piscataway, N.J.) and standard molecular biology methodologies. Overexpression and affinity purification of the resulting GST recombinant proteins was performed as described (Hung et al., 2000).

cDNAs encoding different portions of CPAP were fused in-frame to the C terminus of GFP in a eukaryotic expression vector, pEGFP-C1 (Clontech, Palo Alto, Calif.), or to a prokaryotic expression vector, pET24(a)+ (Novagen, Madison, Wis.) using standard molecular biology methodologies.

Five synthetic peptides (N, H2, C1, C2, and M), corresponding to amino acid residues 310–329 (peptide N), 327–362 (peptide H2), 363–392 (peptide C1), 393–423 (peptide C2), and 320–390 (peptide M) of CPAP (SEQ ID NO:1) were synthesized and FPLC purified by Advanced ChemTech Inc. (Louisville, Ky.) or by Genemed Synthesis Inc. (South San Francisco, Calif.).

In vitro Centrosome-dependant Microtubule Nucleation Assay

Isolation of centrosomes and microtubule nucleation tests were performed as described (Hung et al., 2000). To investigate the effect of different GST-truncated CPAP fusion proteins on microtubule nucleation, purified centrosomes (4 µl per reaction) were pre-incubated with the various truncated GST-CPAP fusion proteins or FPLC purified synthetic peptides for 10 min at 4° C. The reaction mixtures were then incubated in 65 µl RG1 buffer (80 mM PIPES, pH 6.8, 1 mM EGTA, 1 mM MgCl$_2$, and 1 mM GTP) containing 125 µg bovine brain tubulin (Cytoskeleton, Denver, Colo.) for 4 min at 37° C.

Microtubules present in the reaction mixtures were fixed in 200 µl 1% glutaraldehyde in RG1 buffer, sedimented onto acid-treated coverslips, and subjected to immunofluoresence analysis using anti-α-tubulin monoclonal antibodies N356 (Amersham, Piscataway, N.J.) or FITC-conjugated anti-α-tubulin monoclonal antibodies (DM1A-FITC; Sigma, Saint Louis, Mo.). Truncated GST-CPAP proteins were detected using an anti-GST polyclonal antibody (Molecular Probes, Cincinnati, Ohio). The extent of microtubule assembly in each reaction was determined microscopically by comparing the extent of microtubule formation on each coverslip. Decreased microtubule formation in reactions comprising polypeptides derived from CPAP indicated the ability of such polypeptides to inhibit centrosome-dependent microtubule assembly.

Microtubule Depolymerization Assay

In this assay, centrosomes are omitted from the above reaction mixtures to determine the effects of various truncated GST-CPAP proteins or synthetic peptides on microtubule polymerization in the absence of centrosomes. Polymerized microtubules were stained using FITC-conjugated anti-α-tubulin monoclonal antibodies, as above. Nocodazole (15 µM) was added to some reactions mixtures as a positive control for microtubule depolymerization. A reduction in the amount of polymerized microtubules in reaction mixtures receiving truncated GST-CPAP proteins or synthetic peptides indicated that such truncated GST-CPAP proteins or synthetic peptides possessed microtubule destabilizing activity.

In vitro Microtubule Sedimentation Assay

Bovine brain α/β tubulin (15 µM; Cytoskeleton Inc., Denver, Colo.) was pre-incubated with various amounts of truncated GST-CPAP proteins in a 50 µl reaction mixture comprising RG1 buffer (see Example 2) for 30 min at 37° C. Tubulin polymerization was initiated by adding 50 µl GMRG buffer (RG1 buffer supplemented with 12 mM $MgCl_2$ and 50% glycerol), then incubating the reaction mixtures at 37° C. for 1.5 hr.

The reaction mixtures were then subjected to centrifugation at 300,000×g for 15 min at 37° C., in a TL-100 ultracentrifuge (Beckman Instruments, Fullerton, Calif.). Supernatants (S) and pellets (P) were analyzed by SDS-PAGE followed by staining with Coomassie blue.

In experiments containing taxol, microtubules were pre-polymerized using 25 µM paclitaxel (taxol) for 10 min at 37° C. in RG1 buffer supplemented with 4 mM $MgCl_2$, 4 mM ATP, and 4 mM GTP. GST-PN2-2 or GST-PN2-3 recombinant proteins were then added to the pre-polymerized microtubules and incubated for an additional 20 min at 37° C. Following incubation, the reaction mixtures were subjected to centrifugation over a 50 µl glycerol cushion (50% glycerol, 10 µM taxol, and 2 mM GTP in RG1 buffer) at 100,000×g for 30 min at 37° C., in a TL-100 ultracentrifuge. The samples were then resolved by SDS-PAGE. Increased tubulin in the supernatant fractions (and a corresponding decrease in tubulin in the pellet fractions) was indicative of microtubule-destabilizing activity in the reaction mix.

Cell Culture and Transfection

HeLa cells were maintained in DMEM supplemented with 10% fetal bovine serum. cDNA clones encoding different portions of CPAP were subcloned, in an appropriate reading frame, into the CMV promoter-driven EGFP-C1 expression vector (Clontech, Palo Alto, Calif.). Transient transfections were performed using Lipofectamine 2000 (Invitrogen, Carlsbad, Calif.) according to the manufacturer's instructions.

Cold Treatment, Immunofluorescence and Confocal Microscopy

HeLa cells were grown on coverslips for at least 24 hr. Cold treatment was performed by incubating the cells at 4° C. for 1 hr, then replacing the cold medium with medium warmed to 30° C. and incubating the cells for 2 min at 30° C. The cells were then fixed with 1% formaldehyde for 30 min at room temperature.

The fixed cells were incubated in the presence of anti-α-tubulin monoclonal antibodies (N356, Amersham, Piscataway, N.J.) and anti-γ-tubulin polyclonal antibodies (Sigma, Saint Louis, Mo.). Bound anti-α-tubulin monoclonal antibodies (N356) were detected with Alexa 568, a Texas Red-conjugated goat anti-mouse IgG, or Alexa 647, a far-red fluorophore-conjugated goat anti-mouse IgG. Bound anti-γ-tubulin polyclonal antibodies were detected with Alexa 568 (Molecular Probes Inc.). The resulting colorimetric signals were detected using a laser scanning confocal system (MRC 1000, Bio-Rad Laboratories, Hercules, Calif.).

The effect of various polypeptides derived from CPAP was determined by evaluating the amounts of mitotic spindle formation in the transfected cells. Decreased mitotic spindle formation indicated the presence of an activity that inhibited microtubule formation or destabilized microtubules.

Flow Cytometric Analysis

Transfected HeLa cells were harvested 48 hr following transfection. Both the adherent cells and non-adherent cells present in the culture supernatants were collected and subjected to centrifugation. The resulting cell pellets were resuspended in PBS then fixed in 1% formaldehyde at 4° C. for 30 min. Following fixation, the cells were collected by centrifugation, washed, and resuspended in 70% cold ethanol. The resuspended cells were either stored at −20° C. overnight or immediately used for FACS analysis.

FACS analysis was performed by collecting the fixed cells by centrifugation and resuspending the cells in DNA staining solution (100 µg/ml propidium iodide, 0.1% Triton X, and 100 µM EDTA in PBS) for 30 min at room temperature. Cell cycle analysis was performed on a FACS Calibur (Becton-Dickinson, Mountain View, Calif.) with the signal gated to measure only GFP fluorescence. Ten thousand events were acquired and the percentages of cells in $G_0/G_1$, S, and $G_2/M$ were determined using the ModfitLT software (version 2.0, Verity Software House, Inc., Topsham, Me.). The results of the FACS analysis are shown in FIG. 5. The apparent accumulation of cells with two genome copies (i.e., twice the genetic material of $G_0/G_1$ cells) is indicative of cell cycle arrest after DNA synthesis but prior to mitosis.

While this invention has been particularly shown and described with references to preferred embodiments thereof, it will be understood by those skilled in the art that various changes in form and details may be made therein without departing from the spirit and scope of the invention as defined by the appended claims.

Example 1

Structure-Function Analysis of CPAP

To determine the activity of various regions of CPAP, polynucleotide sequences encoding truncated forms of the CPAP polypeptide were cloned into a GST-expression vector (PGEX-2T; Amersham, Piscataway, N.J.) for expression of GST-truncated CPAP polypeptides. A schematic diagram of the various portions of CPAP that were cloned into the expression vector is shown in FIG. 1A.

The resulting GST-tagged polypeptides were affinity purified. FIG. 1B shows a Coomassie-stained polyacrylamide gel on which the affinity-purified polypeptides were analyzed. These GST-truncated CPAP proteins were then tested for their ability to affect microtubule formation in a nucleation assay with purified centrosomes.

As shown in FIG. 1C and Table 1, the formation of microtubule asters (i.e., a radial array of microtubules arising from a centrosome) from the purified centrosomes was inhibited by the GST-CM (corresponding to amino acid residues 132–607 of CPAP) and GST-PN2 (corresponding to amino acid residues 132–422 of CPAP) polypeptides but not by the other GST-truncated CPAP proteins tested in the experiment. Microtubule formation was scored as "low": little or no microtubule formation; "intermediate": moderate microtubule formation; or "high": a high degree of microtubule formation.

TABLE 1

Centrosome-dependent microtubule nucleation in vitro in the presence of polypeptides comprising portions of CPAP

|  | Low | Intermediate | High |
| --- | --- | --- | --- |
| PBS |  |  | X |
| GST-PN1 |  |  | X |
| GST-PN2 | X |  |  |
| GST-A5N |  |  | X |
| GST-CM | X |  |  |
| GST-A5M2-1 |  |  | X |

TABLE 1-continued

Centrosome-dependent microtubule nucleation in vitro in the presence of polypeptides comprising portions of CPAP

|  | Low | Intermediate | High |
|---|---|---|---|
| GST-A5M2-2 |  |  | X |
| GST-A5M2-3 |  |  | X |
| GST-A5C |  |  | X |

This result suggests that the PN2 region, present only in the GST-PN2 and GST-CM polypeptides, possessed the ability to inhibit centrosome-dependent microtubule nucleation in vitro. Quantitative analysis of the inhibitory effect observed in the in vitro assay is shown in FIG. 1D.

Example 2
Structure-Function Analysis of PN2

Figure 2:
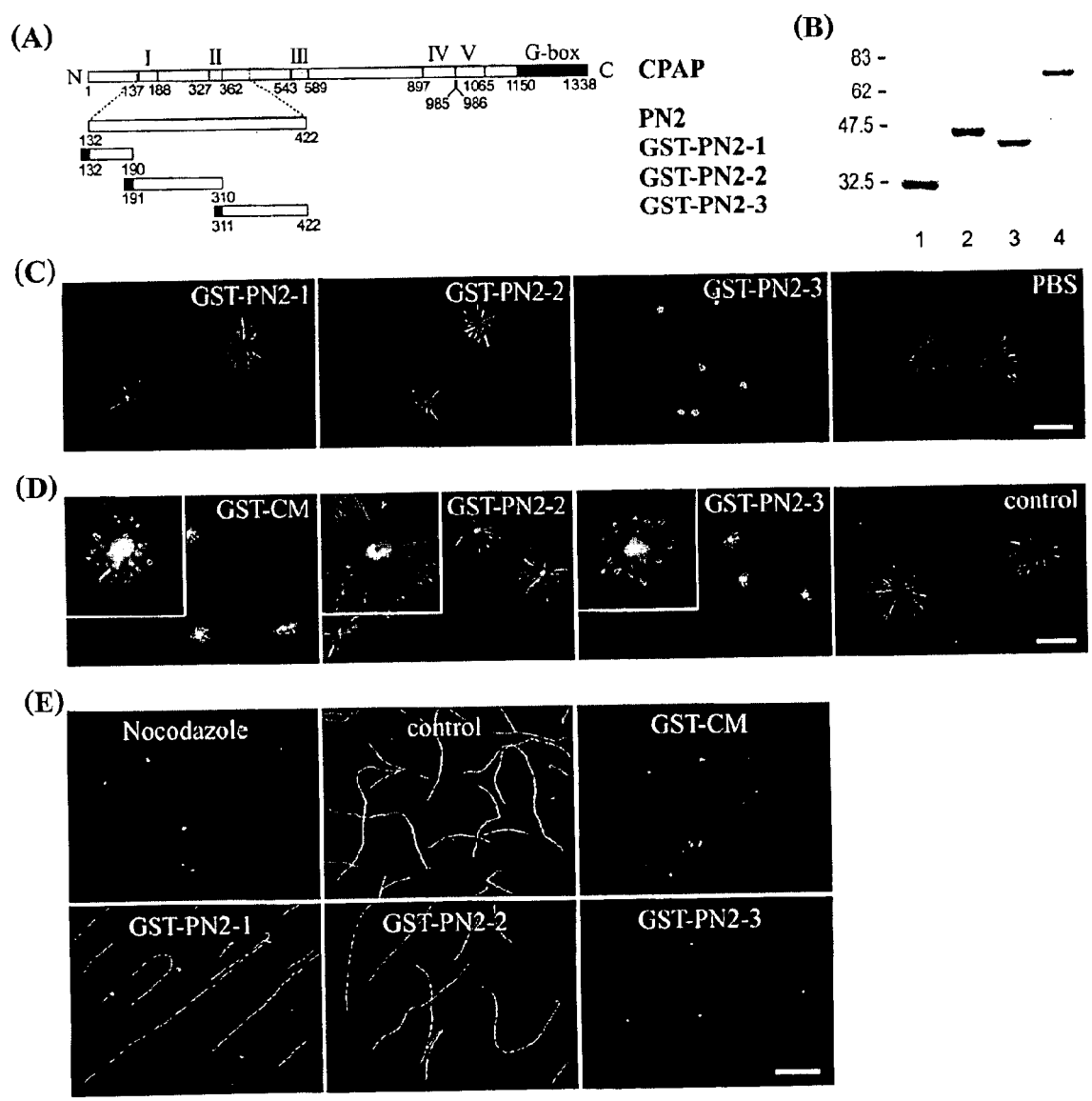
FIG. 2 shows inhibition of microtubule nucleation by portions of the PN2 domain of CPAP. (A) Diagram depicting cDNA constructs encoding various portions of the PN2 domain of CPAP. (B) Coomassie-stained polyacrylamide gel showing affinity-purified GST-truncated PN2 CPAP fusion proteins. (C and D) Results of an in vitro microtubule nucleation assay showing the effect of truncated PN2 CPAP fusion proteins on microtubule nucleation. (E) Results of an in vitro microtubule destabilization assay performed in the absence of centrosomes and in the presence of truncated PN2 CPAP fusion proteins.

To more precisely define the region of PN2 that was responsible for inhibiting centrosome-dependent microtubule nucleation, expression vectors were constructed to express GST-fusion polypeptides comprising one of three sub-regions of PN2. The resulting expression vectors, and the respective polypeptides they encoded, were designated PN2-1, PN2-2, and PN2-3 (FIG. 2A). These polypeptides were expressed and purified (FIG. 2B), then tested for the ability to inhibit centrosome-dependent microtubule nucleation in vitro. As shown in FIG. 2C–2E and Table 2, only GST-PN2-3 (corresponding to residues 311–422 of CPAP) possessed the ability to inhibit microtubule assembly, indicating that the portion of PN2 necessary to inhibit centrosome-dependent microtubule nucleation resides in the PN2-3 region.

TABLE 2

Centrosome-dependent microtubule nucleation in vitro in the presence of polypeptide comprising portions of PN2

|  | None/low | Intermediate | High |
|---|---|---|---|
| PBS |  |  | X |
| GST-PN2-1 |  |  | X |
| GST-PN2-2 |  |  | X |
| GST-PN2-3 | X |  |  |

The CPAP polypeptide comprises five α-helical coiled-coil motifs, designated I to V, which are punctuated by a helix-disrupting proline residue (Hung et al., 2000; FIG. 3A). The PN2-3 of CPAP comprises both an α-helical domain (residues 327–362) and a non-helical structure (residues 363–422). To examine the role of this α-helical structure, the PN2-3 polypeptide was further divided into three sub-regions that comprised either the α-helical motif (PN2-3N), the non-helical motif (PN2-3C), or both (PN2-3M) (FIG. 3A).

GST-fusion polypeptides comprising PN2-3N, PN2-3C, or PN2-3M were expressed and purified (FIG. 3B), and tested in the above centrosome-dependent microtubule nucleation assay. As shown in Table 3, GST-PN2-3 showed the greatest level of inhibition of microtubule nucleation from the centrosomes, while GST-PN2-3M and GST-PN2-3C exhibited less inhibition. Accordingly, the polypeptides inhibited microtubule nucleation from the centrosomes with the following relative level of efficacy: GST-PN2-3>GST-PN2-3M>GST-PN2-3C. No inhibition was observed in the case of GST-PN2-3N, which comprises only the α-helical motif (FIG. 3C and Table 3). Together, these results suggested that both the α-helical and the non-helical structures in PN2-3 are required for full inhibition of microtubule nucleation from the centrosomes.

TABLE 3

Centrosome-dependent microtubule nucleation in vitro in the presence of polypeptide comprising portions of PN2-3

|  | None/low | Intermediate | High |
|---|---|---|---|
| PBS |  |  | X |
| GST-PN2-3 | X |  |  |
| GST-PN2-3N |  |  | X |
| GST-PN2-3M | X |  |  |
| GST-PN2-3C |  | X |  |

To further define the amino acid residues and/or polypeptide secondary structures responsible PN2-3 activity, four residues within the putative amino acid sequence of α-helix domain II (residues 327–362) were mutated, using standard molecular biology techniques, to the known helix-disrupting residue, proline. Specifically, Y341, I346, L348, and L353 (referring to the full-length CPAP polypeptide) were individually mutated to proline, as shown in FIG. 3F. Using the GCG CoilScan program (The Genetics Computer Group package), the probability that the resulting mutated polypeptides would form α-helices was calculated and normalized to that of the "wild-type" PN2-3 polypeptide (i.e., a polypeptide corresponding to amino acid residues 311–422 of SEQ ID NO:1). The predicted probabilities were 0.01, 0.06, 0.00, and 0.06 for Y341P, I346P, L348P, and L353P, respectively, indicating that the mutated polypeptides were less likely to form α-helices than the wild-type PN2-3 sequence.

The mutated PN2-3 polypeptides, along with a PN2-3 polypeptide harboring the "wild-type" CPAP amino acid sequence (i.e., based on SEQ ID NO:1), were expressed using pET vectors (Novagen, Inc., Madison, Wis.) and used in the centrosome-dependent microtubule nucleation assay. As shown in Table 4, only the wild-type and L353P polypeptide showed the ability to inhibit microtubule assembly. These results demonstrate that amino acid residues at positions 341, 346, and 348 (but not 353) are important for PN2-3 activity, presumably due to their structural role in forming or maintaining α-helical domain II.

TABLE 4

Centrosome-dependent microtubule nucleation in vitro in the presence of mutated PN2-3 polypeptides

|  | None/low | Intermediate | High |
|---|---|---|---|
| PBS |  |  | X |
| PN2-3 | X |  |  |
| Y341P |  |  | X |
| I346P |  |  | X |
| L348P |  |  | X |
| L353P | X |  |  |

To assess the inhibitory effect of CPAP-derived polypeptides in the absence of GST amino acid sequences, five peptides were synthesized and tested in the centrosome-dependent microtubule nucleation assay. The peptides included the α-helical motif (peptide H2), the non-helical structure (peptides N, C1, and C2), or both (peptide M). The structural relationship between these synthetic peptides and PN2-3, PN2-3N, PN2-3M, and PN2-3C are shown in FIG. 3A.

As shown in Table 5, peptide M inhibited centrosome-dependent microtubule nucleation in a dose dependent manner, with more inhibition at 40 μM peptide than at 20

μM peptide. No effect was observed using the N, H2, C1, or C2 peptides at 20 μM or 40 μM. Together, these results indicated that both the α-helical and non-helical structures in PN2-3 contribute to the inhibition of microtubule nucleation, and that the presence of GST sequences in the fusion polypeptides was not relevant to the inhibition of microtubule formation.

TABLE 5

Centrosome-dependent microtubule nucleation in vitro in the presence of synthetic peptides comprising portions of PN2-3

|  | None/low | Intermediate | High |
| --- | --- | --- | --- |
| PBS |  |  | X |
| N (20 μM) |  |  | X |
| N (40 μM) |  |  | X |
| H2 (20 μM) |  |  | X |
| H2 (40 μM) |  |  | X |
| M (20 μM) |  | X |  |
| M (40 μM) | X |  |  |
| C1 (20 μM) |  |  | X |
| C1 (40 μM) |  |  | X |
| C2 (20 μM) |  |  | X |
| C2 (40 μM) |  |  | X |

Example 3
Microtubule Depolymerization

A potential mechanism by which the PN2-3 region of CPAP inhibits microtubule formation is through sequestration and disassembly of microtubules, as proposed for OP18/stathmin. To determine whether PN2-3 inhibition functions through a similar mechanism, GST-CM, GST-PN2-1, GST-PN2-2, or GST-PN2-3 were added to microtubule nucleation reactions, as above, except that centrosomes were absent in the reactions (see Example 2). Nocodazole, a known microtubule-depolymerization drug, was used a positive control. Polymerized microtubules were disassembled in the presence of GST-CM, GST-PN2-3, peptide M, or nocodazole, while no such effect was observed in the presence of GST-PN2-1 or GST-PN2-2 (data not shown). These results thus indicate that the CM and PN2-3 polypeptides of CPAP cause microtubules to disassemble in the absence of centrosomes.

Figure 4:
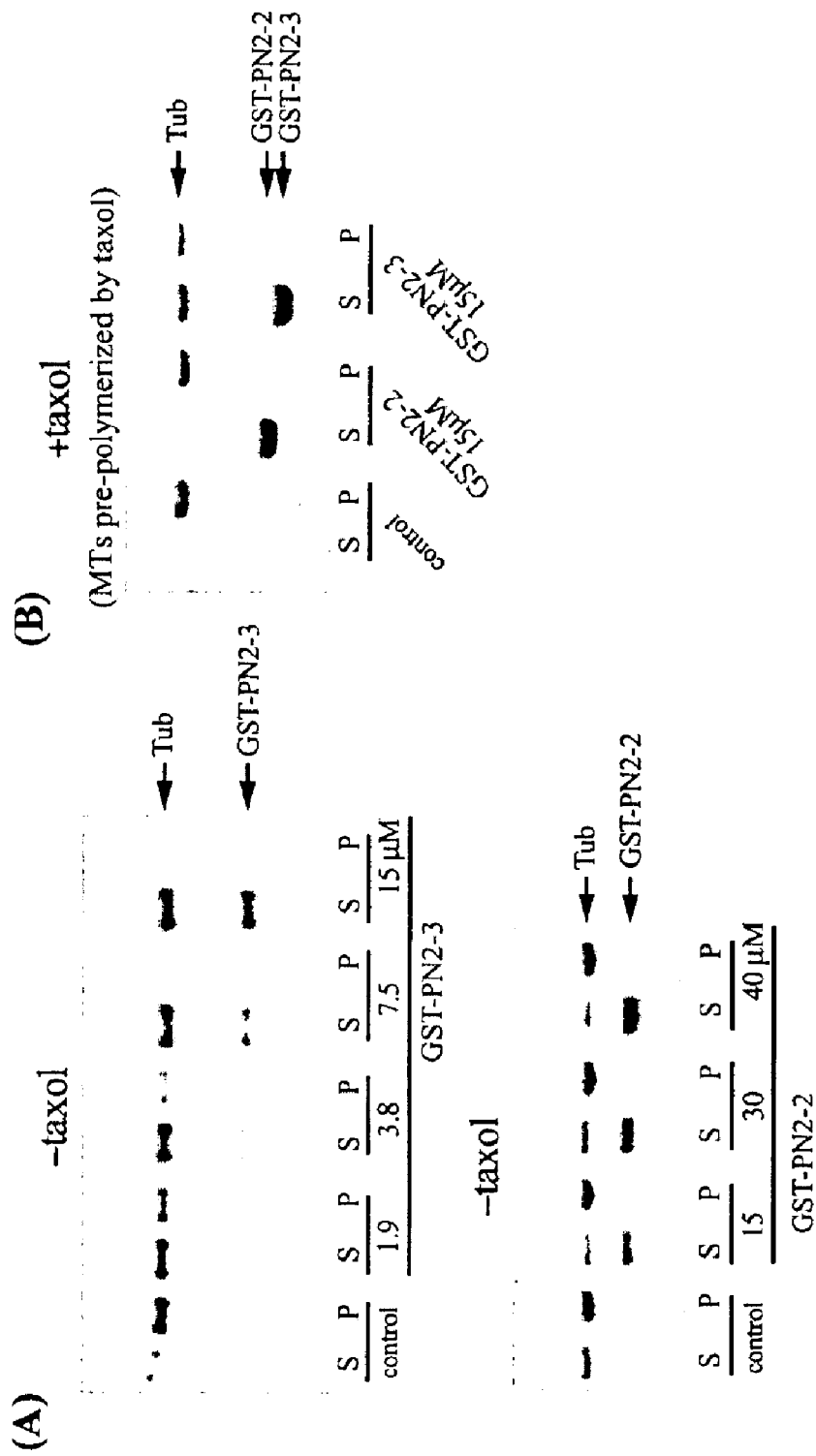
FIG. 4 shows the results of microtubules sedimentation assays. (A) Purified tubulins were incubated with various amounts (as indicated) of GST-PN2-3 (top panel) or GST-PN2-2 (bottom panel). Control samples received no CPAP-derived polypeptides (first two lanes of each panel). The supernatants (S) and pellets (P) were analyzed by SDS-PAGE following electrophoresis. (B) Similar to (A) with the addition of taxol to stabilize the microtubules.

Microtubule disassembly was confirmed using the microtubule sedimentation assay. Following centrifugation of the reaction mixtures, relatively soluble tubulin monomers and small multimers are found in the supernatant, while relatively insoluble polymerized tubulin is found in the pellet. To assay the ability of PN2-3-containing polypeptides to destabilize microtubules, reactions comprising 15 μM tubulin were incubated in the presence of increasing amounts of GST-PN2-3 (1.9, 3.8, 7.5, and 15 μM) or GST-PN2-2 (15, 30, or 40 μM), or in the absence of CPAP-derived polypeptides (control; FIG. 4A).

In control reactions in which PN2-derived polypeptides were not present, most tubulin was found in polymerized form in the pellet (first two lanes of each panel). However, the addition of the GST-PN2-3 to the reaction mixtures increased the amount of soluble tubulin, present in the supernatant, in a dose-dependent manner, indicating that tubulin polymers were destabilized or disassembled by PN2-3. As little as 1.9 μM GST-PN2-3 caused a detectable increase in the amount of soluble tubulin, while 3.8 μM resulted in the majority of the tubulin being converted to soluble form. Insoluble tubulin was further reduced when the reaction mixtures were incubated with 7.5 μM PN2-3 and was barely detectable with 15 μM (equimolar with respect to tubulin in the mixture) PN2-3.

In contrast, even 40 μM GST-PN2-2 had little effect on the distribution of tubulin in the supernatant and pellet. These results indicate that the activity of the PN2-3 polypeptide increased the amount of soluble tubulin present in the centrosome-free reactions.

Example 4
PN2-3 Destabilizes Taxol-stabilized Microtubules

A similar result was also observed in taxol-stabilized microtubules (FIG. 4B). Taxol stabilizes polymerized microtubules such that soluble tubulin is virtually undetectable in the reaction mixture. The presence of 15 μM GST-PN2-3, but not GST-PN2-2, resulted in most of the tubulin being converted to a soluble form (FIG. 4B), indicating that PN2-3, corresponding to amino acid residues 311–422 of CPAP, has the ability to sequester and destabilize microtubules in vitro, in the absence or presence of a microtubule stabilizing substance, such as taxol.

Example 5
Microtubule Destabilization in Cultured Cells

To determine whether CPAP destabilizes microtubules in cells, a series of expression vectors was constructed for expressing green fluorescent protein (GFP)-tagged portions of the CPAP polypeptide, or a GFP-tagged full-length polypeptide. HeLa cells were transiently transfected with the GFP-expression vectors, then cold-treated to increase their sensitivity to microtubule destabilization. As summarized in Table 6, the expression of GFP-CPAP-fl (comprising the full-length CPAP polypeptide, residues 1–1338), GFP-CM (comprising CPAP residues 132–607), or GFP-PN2-3 (comprising CPAP residues 311–422), significantly inhibited microtubule reassembly in cold-treated mitotic cells. These polypeptides localized to mitotic centrosomes but were also present in the cytosol (data not shown).

TABLE 6

Cell-based assay for CPAP activity

|  | None/low | Intermediate | High |
| --- | --- | --- | --- |
| PBS |  |  | X |
| GFP-CPAP-fl | X |  |  |
| GFP-CM | X |  |  |
| GFP-2-3 | X |  |  |
| GFP-A5C |  |  | X |
| GFP-PN2-1 |  |  | X |
| GFP-PN2-2 |  |  | X |
| GFP-PN1 |  |  | X |
| GFP-A5N |  |  | X |
| GFP-A5M2 |  |  | X |
| GFP-CPAP-fl* |  |  | X |

*reduced expression perhaps due to a lower copy number of the construct being transfected into the cells In contrast, no significant inhibition of microtubule reassembly was observed in cells transfected with GFP-A5C (CPAP residues 1070–1338); GFP-PN2-1 (residues 132–190); GFP-PN2-2 (residues 191–310); GFP-PN1 (residues 1–132); GFP-A5N (residues 423–607); or GFP-A5M2 (residues 607–1070), or in cells transfected with expression vectors that expressed lower levels of GFP-CPAP-fl. In the latter cells, GFP-CPAP was detected on the mitotic centrosomes, but only weakly in the cytosol (not shown). Similar results were also obtained using 293 and SiHa cells (not shown). Taken together, these results showed that the PN2-3 region of CPAP inhibited microtubule reassembly from the centrosome in cold-treated cells, providing evidence that CPAP functions as a microtubule destabilizer in cells.

Example 6
Cell Cycle Arrest

To determine whether overexpression of the PN2-3 polypeptide induces cell cycle arrest, HeLa cells were transiently transfected with the above GFP-PN2-3 expression vector, or a control plasmid encoding only GFP, then analyzed by flow cytometry, as described in Examples 5 and 6. Based on the DNA content, as determined by propidium iodine staining, cells transfected with the GFP-PN2-3 expression vector (but not cells transfected with the control plasmid) showed progressive accumulation in $G_2/M$ (right-most peaks), with a corresponding decrease of cells in $G_0/G_1$ (left-most peaks)(FIG. 5). GFP-PN2-3-transfected cells also exhibited a change in morphology (to round cells) and stopped proliferating (data not shown). These cell cycle and morphological changes were not observed in cells transfected with the expression vector expressing only GFP, indicating that the PN2-3 polypeptide was responsible for the arrest in mitosis at $G_2/M$ and the accompanying morphological changes.

What is claimed is:

1. An isolated polypeptide selected from the group consisting of:

a) a polypeptide of amino acid residues 311–422 of SEQ ID NO:1; and b) a polypeptide that shares 95% sequence identity with residues 311–422 of SEQ ID NO:1 and has microtubule destabilizing activity.

2. A recombinant polypeptide comprising the polypeptide of claim 1, with the proviso that the polypeptide is not CPAP.

3. A method for destabilizing microtubules in a cell, comprising providing to the cell a polypeptide in a sufficient amount to destabilize microtubules in the cell, wherein the polypeptide is selected from a polypeptide of claim 1.

4. A method for inhibiting proliferation of a cell, comprising providing to the cell a polypeptide in a sufficient amount to inhibit proliferation of the cell, wherein the polypeptide is selected a polypeptide of claim 1.

5. A method for treating a tumor, comprising providing to cells of the tumor a polypeptide delivered by direct injection of said tumor cells, administered in a sufficient amount to inhibit proliferation of the cell, wherein the polypeptide is selected from a polypeptide of claim 1.

6. A method for screening drugs that modulate microtubule assembly, comprising contacting microtubules with a protein that comprises the polypeptide of claim 1, in the presence and absence of a drug, and determining the effect of the drug on microtubule assembly.

* * * * *